(12) United States Patent
Moll et al.

(10) Patent No.: US 10,702,348 B2
(45) Date of Patent: Jul. 7, 2020

(54) SURGICAL SYSTEM WITH CONFIGURABLE RAIL-MOUNTED MECHANICAL ARMS

(71) Applicant: Auris Health, Inc., Redwood City, CA (US)

(72) Inventors: Frederic H. Moll, San Francisco, CA (US); Alan Lau Yu, Union City, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/195,206

(22) Filed: Nov. 19, 2018

(65) Prior Publication Data
US 2019/0083183 A1    Mar. 21, 2019

Related U.S. Application Data

(63) Continuation of application No. 15/094,179, filed on Apr. 8, 2016, now Pat. No. 10,159,533.
(Continued)

(51) Int. Cl.
*A61B 34/30* (2016.01)
*A61B 50/10* (2016.01)
(Continued)

(52) U.S. Cl.
CPC .......... *A61B 34/30* (2016.02); *A61B 1/00149* (2013.01); *A61B 34/00* (2016.02);
(Continued)

(58) Field of Classification Search
CPC ... A61B 34/30; A61B 50/10; A61B 2090/571; A61B 1/00149; A61G 13/06;
(Continued)

(56) References Cited

U.S. PATENT DOCUMENTS

| | | |
|---|---|---|
| 4,878,494 A | 11/1989 | Phillips et al. |
| 5,013,018 A | 5/1991 | Sicek |

(Continued)

FOREIGN PATENT DOCUMENTS

| | | |
|---|---|---|
| CN | 202314134 U | 7/2012 |
| WO | WO 10/068005 | 6/2010 |

OTHER PUBLICATIONS

International search report and written opinion dated Jul. 13, 2016 for PCT/US2016/026783.

*Primary Examiner* — Nicholas F Polito
(74) *Attorney, Agent, or Firm* — Knobbe, Martens, Olson & Bear, LLP

(57) ABSTRACT

A robotic surgical system comprises a horizontal platform to support a patient, a rail positioned about the horizontal platform, a carriage operatively coupled to and configured to translate along the rail, and a robotic arm operatively coupled to the carriage and translated about the patient by the rail. The robotic arm is configured to operate on the patient in a variety of positions provided by the translating carriage. The rail provides a rounded path for the carriage, such as a U-shaped path. The U-shaped path may comprise a first leg and a second leg, the first leg longer than the second leg. Furthermore, the system may comprise a plurality of carriages operatively coupled to the rail and a plurality of robotic arms. Also, the system may further comprise a central base which the horizontal platform can articulate relative to, such as by translating horizontally or vertically, rotating, or titling.

21 Claims, 20 Drawing Sheets

Related U.S. Application Data

(60) Provisional application No. 62/145,418, filed on Apr. 9, 2015.

(51) Int. Cl.

| | | |
|---|---|---|
| *A61B 90/50* | (2016.01) | |
| *A61G 13/06* | (2006.01) | |
| *A61G 13/10* | (2006.01) | |
| *A61B 34/20* | (2016.01) | |
| *A61B 34/00* | (2016.01) | |
| *A61B 1/00* | (2006.01) | |
| *A61G 13/04* | (2006.01) | |
| *A61B 90/57* | (2016.01) | |
| *A61B 1/313* | (2006.01) | |
| *A61B 1/267* | (2006.01) | |
| *A61B 1/31* | (2006.01) | |
| *A61B 1/303* | (2006.01) | |
| *A61B 1/307* | (2006.01) | |
| *A61B 1/273* | (2006.01) | |

(52) U.S. Cl.
CPC ............ *A61B 34/20* (2016.02); *A61B 50/10* (2016.02); *A61B 90/50* (2016.02); *A61G 13/04* (2013.01); *A61G 13/06* (2013.01); *A61G 13/10* (2013.01); *A61B 1/2676* (2013.01); *A61B 1/2736* (2013.01); *A61B 1/303* (2013.01); *A61B 1/307* (2013.01); *A61B 1/31* (2013.01); *A61B 1/3132* (2013.01); *A61B 2034/304* (2016.02); *A61B 2090/571* (2016.02); *A61G 13/101* (2013.01)

(58) Field of Classification Search
CPC ...... A61G 13/10; A61G 13/101; A61G 13/00; A61G 13/0036; A61G 13/0045; A61G 13/0054; A61G 13/0063; A61G 13/0072; A61G 13/0081; A61G 13/04; A61G 13/107
See application file for complete search history.

(56) References Cited

U.S. PATENT DOCUMENTS

| | | | |
|---|---|---|---|
| 5,160,106 A | | 11/1992 | Monick |
| 5,259,365 A | | 11/1993 | Nishikori |
| 5,555,897 A | | 9/1996 | Lathrop, Jr. et al. |
| 5,571,072 A | | 11/1996 | Kronner |
| 5,597,146 A | | 1/1997 | Putman |
| 5,762,458 A | | 6/1998 | Wang et al. |
| 5,814,038 A | | 9/1998 | Jensen et al. |
| 5,926,875 A | | 7/1999 | Okamoto et al. |
| 5,944,476 A | | 8/1999 | Bacchi et al. |
| 6,170,102 B1 | | 1/2001 | Kreuzer |
| 6,202,230 B1 | * | 3/2001 | Borders ............ A61G 13/0009 5/613 |
| 6,620,174 B2 | | 9/2003 | Jensen et al. |
| 6,676,669 B2 | | 1/2004 | Charles et al. |
| 6,804,581 B2 | | 10/2004 | Wang |
| 7,025,761 B2 | | 4/2006 | Wang et al. |
| 7,074,179 B2 | | 7/2006 | Wang et al. |
| 7,763,015 B2 | | 7/2010 | Cooper et al. |
| 7,789,874 B2 | | 9/2010 | Yu et al. |
| 7,850,642 B2 | | 12/2010 | Moll et al. |
| 7,963,288 B2 | | 6/2011 | Rosenberg et al. |
| 7,972,298 B2 | | 7/2011 | Wallace et al. |
| 7,974,681 B2 | | 7/2011 | Wallace et al. |
| 7,976,539 B2 | | 7/2011 | Hlavka et al. |
| 7,979,157 B2 | | 7/2011 | Anvari |
| 7,996,110 B2 | | 8/2011 | Lipow et al. |
| 8,005,537 B2 | | 8/2011 | Hlavka et al. |
| 8,021,326 B2 | | 9/2011 | Moll et al. |
| 8,052,636 B2 | | 11/2011 | Moll et al. |
| 8,108,069 B2 | | 1/2012 | Stahler et al. |
| 8,142,420 B2 | | 3/2012 | Schena |
| 8,146,874 B2 | | 4/2012 | Yu |
| 8,172,747 B2 | | 5/2012 | Wallace et al. |
| 8,190,238 B2 | | 5/2012 | Moll et al. |
| 8,230,863 B2 | | 7/2012 | Ravikumar et al. |
| 8,257,303 B2 | | 9/2012 | Moll et al. |
| 8,311,626 B2 | | 11/2012 | Hlavka et al. |
| 8,343,096 B2 | | 1/2013 | Kirschenman et al. |
| 8,348,931 B2 | | 1/2013 | Cooper et al. |
| 8,394,054 B2 | | 3/2013 | Wallace et al. |
| 8,400,094 B2 | | 3/2013 | Schena |
| 8,409,136 B2 | | 4/2013 | Wallace et al. |
| 8,409,172 B2 | | 4/2013 | Moll et al. |
| 8,414,598 B2 | | 4/2013 | Brock et al. |
| 8,425,404 B2 | | 4/2013 | Wilson et al. |
| 8,469,945 B2 | | 6/2013 | Schena |
| 8,498,691 B2 | | 7/2013 | Moll et al. |
| 8,506,556 B2 | | 8/2013 | Schena |
| 8,512,353 B2 | | 8/2013 | Rosielle et al. |
| 8,515,576 B2 | | 8/2013 | Lipow et al. |
| 8,617,102 B2 | | 12/2013 | Moll et al. |
| 8,641,698 B2 | | 2/2014 | Sanchez et al. |
| 8,801,661 B2 | | 8/2014 | Moll et al. |
| 8,897,920 B2 | | 11/2014 | Wang et al. |
| 8,911,429 B2 | | 12/2014 | Olds et al. |
| 8,926,603 B2 | | 1/2015 | Hlavka et al. |
| 8,960,622 B2 | | 2/2015 | von Pechmann et al. |
| 8,968,333 B2 | | 3/2015 | Yu et al. |
| 8,974,408 B2 | | 3/2015 | Wallace et al. |
| 9,023,060 B2 | | 5/2015 | Cooper et al. |
| 9,078,686 B2 | | 7/2015 | Schena |
| 9,259,281 B2 | | 2/2016 | Griffiths et al. |
| 9,314,306 B2 | | 4/2016 | Yu |
| 9,326,822 B2 | | 5/2016 | Lewis et al. |
| 9,358,076 B2 | | 6/2016 | Moll et al. |
| 9,408,669 B2 | | 8/2016 | Kokish et al. |
| 9,452,018 B2 | | 9/2016 | Yu |
| 9,457,168 B2 | | 10/2016 | Moll et al. |
| 9,504,604 B2 | | 11/2016 | Alvarez |
| 9,554,865 B2 | | 1/2017 | Olds et al. |
| 9,561,083 B2 | | 2/2017 | Yu et al. |
| 9,566,201 B2 | | 2/2017 | Yu |
| 9,615,889 B2 | | 4/2017 | Jensen |
| 9,622,827 B2 | | 4/2017 | Yu et al. |
| 9,629,682 B2 | | 4/2017 | Wallace et al. |
| 9,636,184 B2 | | 5/2017 | Lee et al. |
| 9,713,499 B2 | | 7/2017 | Bar et al. |
| 9,713,509 B2 | | 7/2017 | Schuh et al. |
| 9,727,963 B2 | | 8/2017 | Mintz et al. |
| 9,737,371 B2 | | 8/2017 | Romo et al. |
| 9,737,373 B2 | | 8/2017 | Schuh |
| 9,744,335 B2 | | 8/2017 | Jiang |
| 9,763,741 B2 | | 9/2017 | Alvarez et al. |
| 9,788,910 B2 | | 10/2017 | Schuh |
| 9,795,454 B2 | | 10/2017 | Seeber et al. |
| 9,820,819 B2 | | 11/2017 | Olson |
| 9,844,412 B2 | | 12/2017 | Bogusky et al. |
| 9,850,924 B2 | | 12/2017 | Vogtherr et al. |
| 9,867,635 B2 | | 1/2018 | Alvarez et al. |
| 9,907,458 B2 | | 3/2018 | Schena |
| 9,918,681 B2 | | 3/2018 | Wallace et al. |
| 9,931,025 B1 | | 4/2018 | Graetzel et al. |
| 9,949,749 B2 | | 4/2018 | Noonan et al. |
| 9,955,986 B2 | | 5/2018 | Shah |
| 9,962,228 B2 | | 5/2018 | Schuh et al. |
| 9,980,785 B2 | | 5/2018 | Schuh |
| 9,993,313 B2 | | 6/2018 | Schuh et al. |
| 9,999,476 B2 | | 6/2018 | Griffiths |
| 10,016,900 B1 | | 7/2018 | Meyer et al. |
| 10,022,192 B1 | | 7/2018 | Ummalaneni |
| 10,080,576 B2 | | 9/2018 | Romo et al. |
| 10,136,959 B2 | | 11/2018 | Mintz et al. |
| 10,145,747 B1 | | 12/2018 | Lin et al. |
| 10,149,720 B2 | | 12/2018 | Romo |
| 10,159,532 B1 | | 12/2018 | Ummalaneni et al. |
| 10,159,533 B2 | | 12/2018 | Moll et al. |
| 10,169,875 B2 | | 1/2019 | Mintz et al. |
| 10,231,867 B2 | | 3/2019 | Alvarez et al. |

(56) References Cited

U.S. PATENT DOCUMENTS

| | | |
|---|---|---|
| 10,524,866 B2 | 1/2020 | Srinivasan et al. |
| 2002/0162926 A1 | 11/2002 | Nguyen |
| 2002/0165524 A1 | 11/2002 | Sanchez et al. |
| 2002/0170116 A1 | 11/2002 | Borders |
| 2003/0191455 A1 | 10/2003 | Sanchez et al. |
| 2004/0243147 A1 | 12/2004 | Lipow |
| 2004/0261179 A1 | 12/2004 | Blumenkranz |
| 2005/0222554 A1 | 10/2005 | Wallace et al. |
| 2006/0069383 A1 | 3/2006 | Bogaerts |
| 2006/0149418 A1* | 7/2006 | Anvari .................. A61G 13/10 700/245 |
| 2006/0200026 A1 | 9/2006 | Wallace et al. |
| 2008/0027464 A1 | 1/2008 | Moll et al. |
| 2008/0039867 A1 | 2/2008 | Feussner |
| 2008/0082109 A1 | 4/2008 | Moll et al. |
| 2008/0167750 A1 | 7/2008 | Stahler |
| 2008/0195081 A1 | 8/2008 | Moll et al. |
| 2008/0218770 A1 | 9/2008 | Moll et al. |
| 2008/0245946 A1 | 10/2008 | Yu |
| 2009/0036900 A1 | 2/2009 | Moll |
| 2009/0062602 A1 | 3/2009 | Rosenberg et al. |
| 2009/0163928 A1 | 6/2009 | Schena |
| 2010/0185211 A1 | 7/2010 | Herman |
| 2010/0204713 A1 | 8/2010 | Ruiz |
| 2010/0286712 A1 | 11/2010 | Won et al. |
| 2011/0028894 A1 | 2/2011 | Foley et al. |
| 2011/0238083 A1 | 9/2011 | Moll et al. |
| 2011/0270273 A1 | 11/2011 | Moll et al. |
| 2012/0191079 A1 | 7/2012 | Moll et al. |
| 2012/0191083 A1 | 7/2012 | Moll et al. |
| 2012/0191086 A1 | 7/2012 | Moll et al. |
| 2012/0241576 A1 | 9/2012 | Yu |
| 2012/0253332 A1 | 10/2012 | Moll |
| 2012/0266379 A1 | 10/2012 | Hushek |
| 2012/0296161 A1 | 11/2012 | Wallace et al. |
| 2013/0041219 A1 | 2/2013 | Hasegawa et al. |
| 2013/0190741 A1 | 7/2013 | Moll et al. |
| 2013/0255425 A1 | 10/2013 | Schena |
| 2013/0338679 A1 | 12/2013 | Rosielle et al. |
| 2014/0142591 A1 | 5/2014 | Alvarez et al. |
| 2014/0180309 A1 | 6/2014 | Seeber et al. |
| 2014/0188132 A1 | 7/2014 | Kang |
| 2014/0249546 A1 | 9/2014 | Shvartsberg et al. |
| 2014/0276391 A1 | 9/2014 | Yu |
| 2014/0276647 A1 | 9/2014 | Yu |
| 2014/0276935 A1 | 9/2014 | Yu |
| 2014/0277333 A1 | 9/2014 | Lewis et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0038981 A1 | 2/2015 | Kilroy et al. |
| 2015/0051592 A1 | 2/2015 | Kintz |
| 2015/0119638 A1 | 4/2015 | Yu et al. |
| 2015/0164594 A1 | 6/2015 | Romo et al. |
| 2015/0164596 A1 | 6/2015 | Romo |
| 2015/0335389 A1 | 11/2015 | Greenberg |
| 2015/0335480 A1 | 11/2015 | Alvarez et al. |
| 2016/0001038 A1 | 1/2016 | Romo et al. |
| 2016/0100896 A1 | 4/2016 | Yu |
| 2016/0157942 A1* | 6/2016 | Gombert et al. ...... B25J 9/1666 606/130 |
| 2016/0235946 A1 | 8/2016 | Lewis et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0338785 A1 | 11/2016 | Kokish et al. |
| 2016/0346052 A1 | 12/2016 | Rosielle et al. |
| 2016/0354582 A1 | 12/2016 | Yu et al. |
| 2016/0374541 A1 | 12/2016 | Agrawal et al. |
| 2016/0374771 A1* | 12/2016 | Mirbagheri ............ A61B 34/35 606/130 |
| 2017/0007337 A1 | 1/2017 | Dan |
| 2017/0007343 A1 | 1/2017 | Yu |
| 2017/0071692 A1 | 3/2017 | Taylor et al. |
| 2017/0071693 A1* | 3/2017 | Taylor .................... A61B 90/50 |
| 2017/0086929 A1 | 3/2017 | Moll et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0135771 A1 | 5/2017 | Auld et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209217 A1 | 7/2017 | Jensen |
| 2017/0215976 A1 | 8/2017 | Nowlin et al. |
| 2017/0215978 A1 | 8/2017 | Wallace et al. |
| 2017/0290631 A1 | 10/2017 | Lee et al. |
| 2017/0304021 A1 | 10/2017 | Hathaway |
| 2017/0325906 A1 | 11/2017 | Piecuch et al. |
| 2017/0333679 A1 | 11/2017 | Jiang |
| 2017/0340353 A1 | 11/2017 | Ahluwalia et al. |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0078439 A1 | 3/2018 | Cagle et al. |
| 2018/0078440 A1 | 3/2018 | Koenig et al. |
| 2018/0079090 A1 | 3/2018 | Koenig et al. |
| 2018/0116758 A1* | 5/2018 | Schlosser ............... A61B 90/50 |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0228528 A1 | 4/2019 | Mintz et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |

(56) References Cited

U.S. PATENT DOCUMENTS

2019/0380787 A1   12/2019  Ye
2019/0380797 A1   12/2019  Yu
2020/0000530 A1    1/2020  DeFonzo
2020/0000533 A1    1/2020  Schuh

* cited by examiner

513

512

511

SURGICAL SYSTEM WITH CONFIGURABLE RAIL-MOUNTED MECHANICAL ARMS

CROSS REFERENCE TO RELATED APPLICATIONS

This application is a continuation of U.S. application Ser. No. 15/094,179, filed Apr. 8, 2016, which claims the benefit of U.S. Provisional Application No. 62/145,418, filed Apr. 9, 2015, each of which is incorporated herein by reference.

The present invention relates to medical instruments, tools, and methods that may be incorporated into a robotic system, such as those disclosed in U.S. patent application Ser. No. 14/523,760, filed Oct. 24, 2014, U.S. Provisional Patent Application No. 62/019,816, filed Jul. 1, 2014, U.S. Provisional Patent Application No. 62/037,520, filed Aug. 14, 2014, and U.S. Provisional Patent Application No. 62/057,936, filed Sep. 30, 2014, the entire contents of which are incorporated herein by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The field of the present invention relates to a robotics platform that may be used in a number of surgical procedures. More particularly, the field of the invention pertains to robotic platforms that enable robotically-controlled tools to perform diagnostic and therapeutic surgical procedures.

BACKGROUND OF THE RELATED ART

Use of robotic technologies presents a number of advantages over traditional, manual surgery procedures. In addition to other advantages, robotic surgeries often allow for greater precision, control, and access. Despite these advantages, however, the pre-existing robotics platforms have built-in limitations that are tied to their structural designs and underpinnings. In the absence of a truly flexible system, hospitals and health care practitioners are forced to acquire a variety of robotic systems in order to robotically perform a variety of procedures. The high capital costs, combined with the relatively specialization of the systems, have slowed adoption of robotics platforms for surgery.

Accordingly, there is a need for a robotics platform that is configurable for a number of procedures.

BRIEF SUMMARY OF THE INVENTION

In general, the present invention provides a medical device that comprises a rail having a rounded path, a carriage configured to translate along the rail, the carriage being operatively coupled to the rail, a robotic arm operatively coupled to the carriage, and a horizontal platform proximate to the rail, wherein the robotic arms are configured to perform medical procedures on a patient on the platform. In one aspect, the rounded path is U-shaped. In one aspect, the U-shaped path comprises of a first leg and a second leg, wherein the first leg is longer than the second leg. In another aspect, the rail is configured around a central base. In one aspect, the central base is shaped like a column.

In another aspect, a horizontal platform is operatively coupled to the top of the base. In one aspect, the rail is disposed below the platform. In one aspect, the rail is around the platform. In one aspect, the arm is configured to be angled over platform.

In another aspect, the platform is a surgical bed, configured to support the weight of a patient. In one aspect, the surgical bed comprises a first part and a second part, wherein the second part is configured to articulate relative to the first part.

In another aspect, the rail is configured around a horizontal platform. In one aspect, the platform is a surgical bed, configured to support the weight of a patient.

In another aspect, the rounded path is circular. In one aspect, the rail is disposed below the platform. In one aspect, the rail is around the platform.

BRIEF DESCRIPTION OF THE DRAWINGS

The invention will be described, by way of example, and with reference to the accompanying diagrammatic drawings, in which.

DETAILED DESCRIPTION OF THE DRAWINGS

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

In clinical applications, the design of the base of the robotics platform often constrains the types of procedures that may be performed by the system. For example, in a system where robotic appendages are only available around the abdomen, urology procedures are precluded from being performed. Likewise, robotic arms below the abdomen may not be useful for laparoscopic procedures. Accordingly, the present invention provides a flexible design such that robotic arms may be delivered to multiple access points in a patient around a surgical bed.

Figure 1:
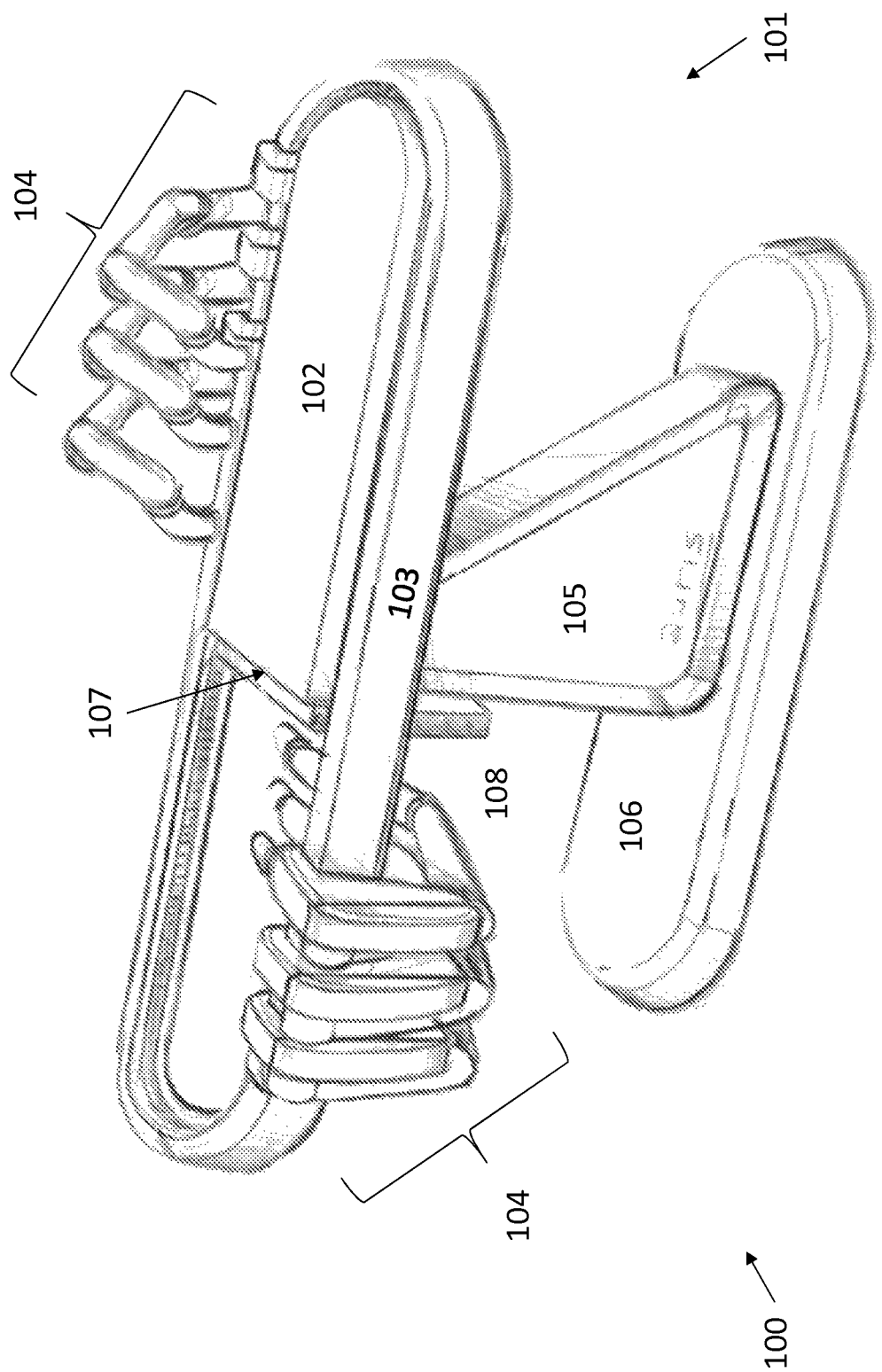
FIG. 1 illustrates a surgical bed with an oval track for robotic arms along the edge of the bed, consistent with an embodiment of the present invention.

FIG. 1 illustrates a surgical bed with an oval track for robotic arms along the edge of the bed, consistent with an embodiment of the present invention. As shown in the isometric view 100 of the robotic system 101, the system 101 comprises of a surgical bed 102, a rail 103 for mechanical arms 104, a support stand 105, and a system base 106. The surgical bed allows for a hinge 107 such that a portion 108 of surgical bed 102 may be declined at a different angle from the rest of the bed. This may be desirable for certain operations, such as when performing a procedure that requires access a patient's lower abdomen, such as ureteroscopy or hysteroscopy.

Encircling the surgical bed 102, the rail 103 provides a structure to slidingly translate the mechanical arms 104 to a desired location around the surgical bed 102. The rail 103, which may be referred to as a "track", and the mechanical arms 104 may be slidingly translated along it in order to facilitate access for the arms. The rail 103 also provides allows for the conveyance and reception of power, controls, fluidics, aspiration to the mechanical arms 104. The rail 103 may be fully circular and surround all sides of the surgical bed 102.

The mechanical arms 104 may be operatively coupled to the rail 103. The mechanical arms may also be robotic. The translation of the mechanical arms 104 may be actuated either manually or robotically. The mechanical arms 104 may be coupled independently to the rail 103 or in groups via a mechanical carriage that may slide around the rail 103. In addition to providing structural support to the mechanical arms 104, the carriage may be used to convey and receive power, controls, fluidics, and aspiration to and from the arms 104 to the rail 103.

In combination or individually, the support stand 105 and the system base 106 may be used to house electronics, fluidics, pneumatics, and aspiration. The electronics may be used from control, localization, navigation of the arms 104. Thus, as a robotically-driven platform, system 101 provides for a comprehensive surgical bed and tool solution that may be used to perform any number of procedures around a patient.

Figure 2:
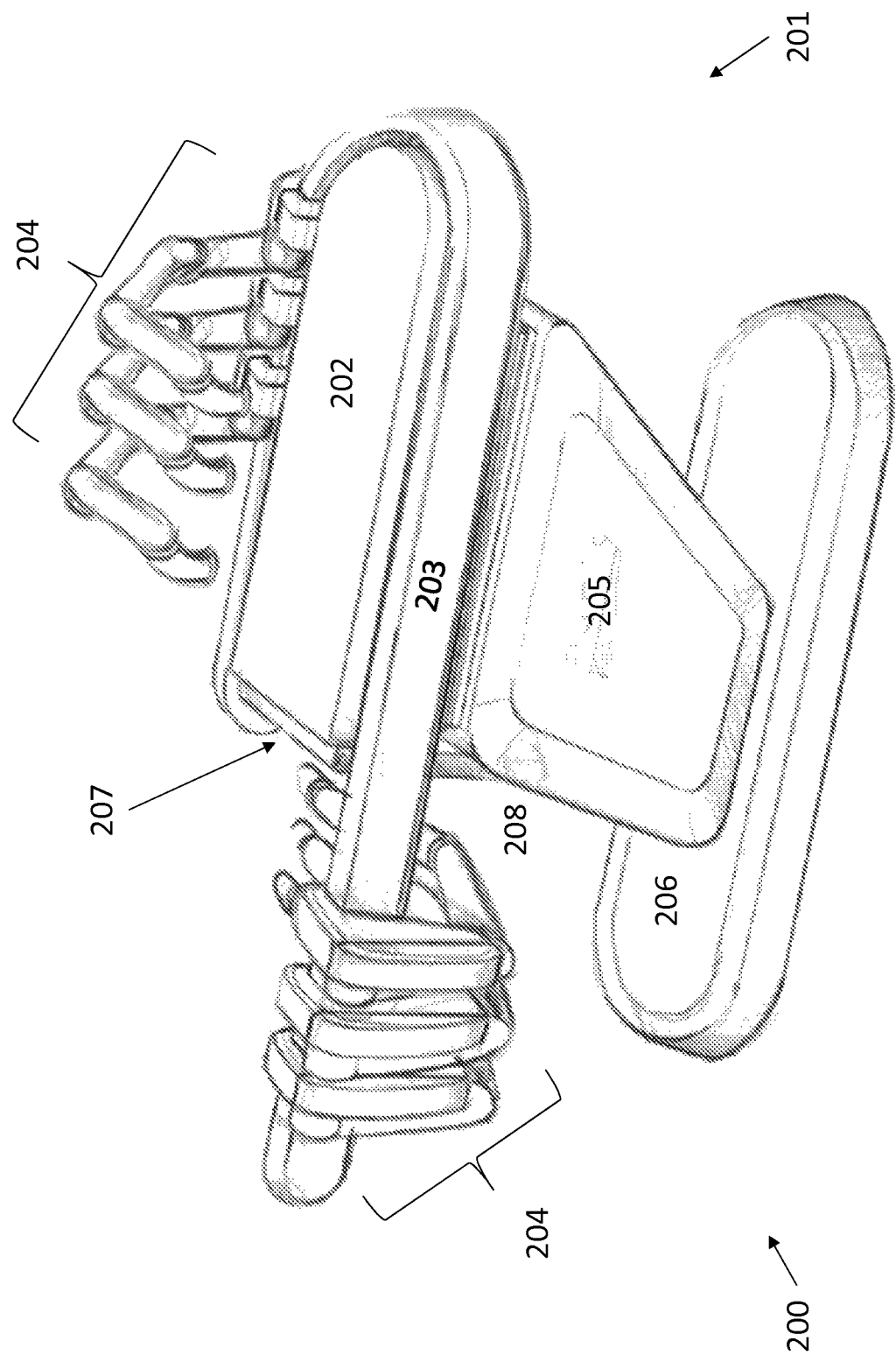
FIG. 2 illustrates a surgical bed with a U-shaped track for robotic arms along the edge of the bed, consistent with an embodiment of the present invention.

FIG. 2 illustrates a surgical bed with a U-shaped track for robotic arms along the edge of the bed, consistent with an embodiment of the present invention. As shown in the isometric view 200 of the robotic system 201, the system 201 comprises of a surgical bed 202, a rail 203 for mechanical arms 204, a support stand 205, and a system base 206. Like in system 101, the surgical bed 202 allows for a hinge 207 such that a portion 208 of surgical bed 202 may be declined at a different angle from the rest of the bed 202. As discussed earlier, this may be desirable for certain operations, such as when performing a procedure that requires access a patient's lower abdomen, such as ureteroscopy, hysteroscopy, or colonoscopy.

Running along the surgical bed 202, the rail 203 provides a structure to slidingly translate the mechanical arms 204 to a desired location around the surgical bed 202. Unlike rail 103, rail 203 uses a U-shape that enhances access the surgical bed 202. This may provide advantages when position the patient and accessing operative sites on a patient's lower abdomen. The longer leg of the rail 203 allows for the mechanical arms to be aligned to convey a medical instrument into the patient by means of a "virtual rail" such as one discussed in the aforementioned patent applications. As before, the rail 203 may be referred to as a "track", and the mechanical arms 204 may be slidingly translated along it in order to facilitate access for the arms. The rail 203 also provides allows for the conveyance and reception of power, controls, fluidics, aspiration to the mechanical arms 204.

In combination or individually, the support stand 205 and the system base 206 may be used to house electronics, fluidics, pneumatics, and aspiration. The electronics may be used from control, localization, navigation of the arms 204. Thus, as a robotically-driven platform, system 201 provides for an improved, comprehensive surgical bed and tool solution that may be used to perform any number of procedures around a patient.

As deployed, the mechanical arms 104 from system 101 and mechanical arms 204 and system 201 are positioned to perform endolumenal procedures to access the access points in the lower abdomen (e.g., urology, ureteroscopy, hysteroscopy, or colonoscopy) and upper abdomen (e.g., bronchoscopy, gastro-intestinal).

Figure 3:
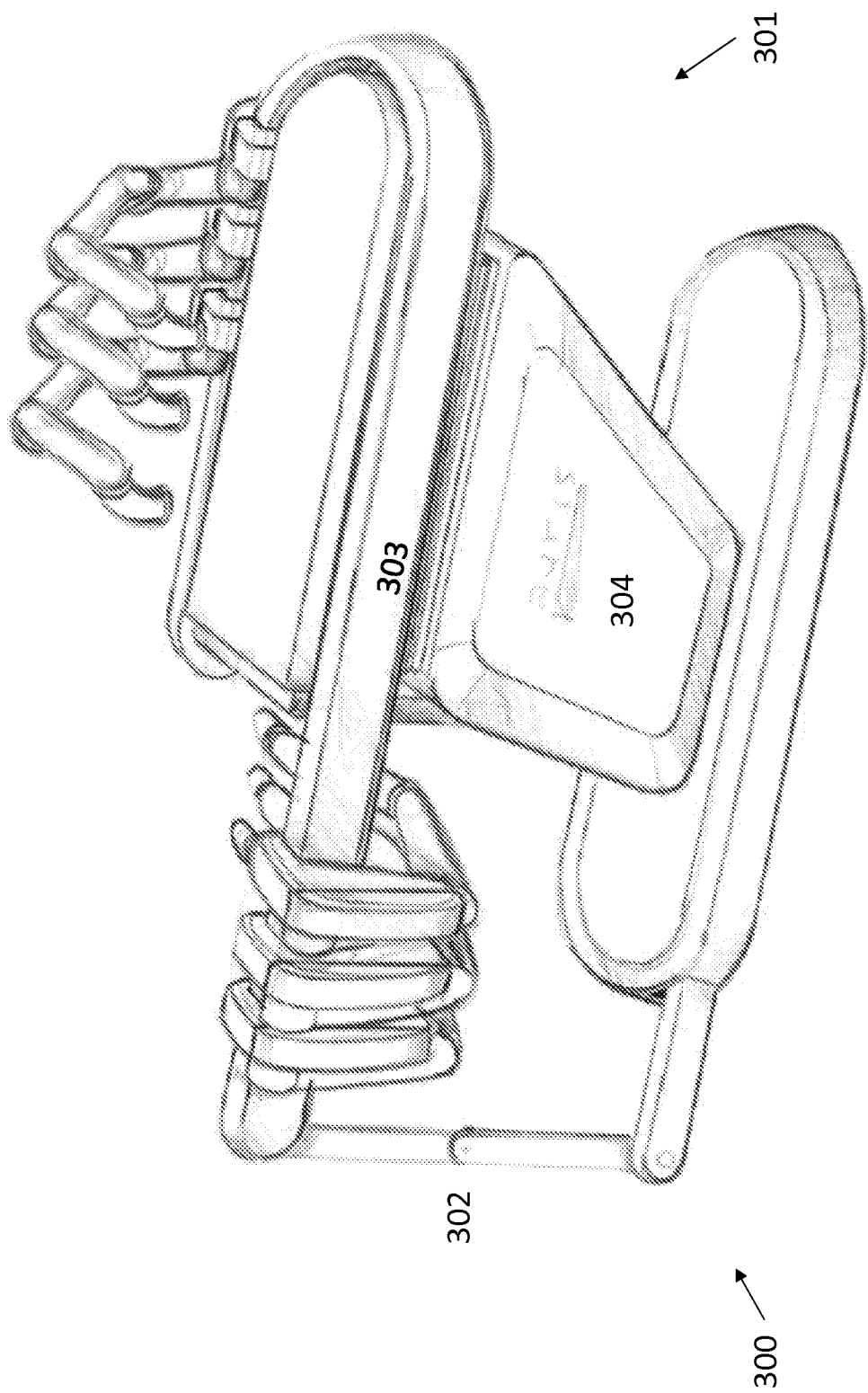
FIG. 3 illustrates an alternative robotics platform to system 201 from FIG. 2.

FIG. 3 illustrates an alternative robotics platform to system 201 from FIG. 2. As shown in isometric view 300, system 301 incorporates all the technologies disclosed with respect to system 201 with the additional vertical translation apparatus 302 that enables control over the vertical height of the rail 303. System 301 thus allows for vertical translation of the rail 303 relative to the support stand 304.

Figure 4:
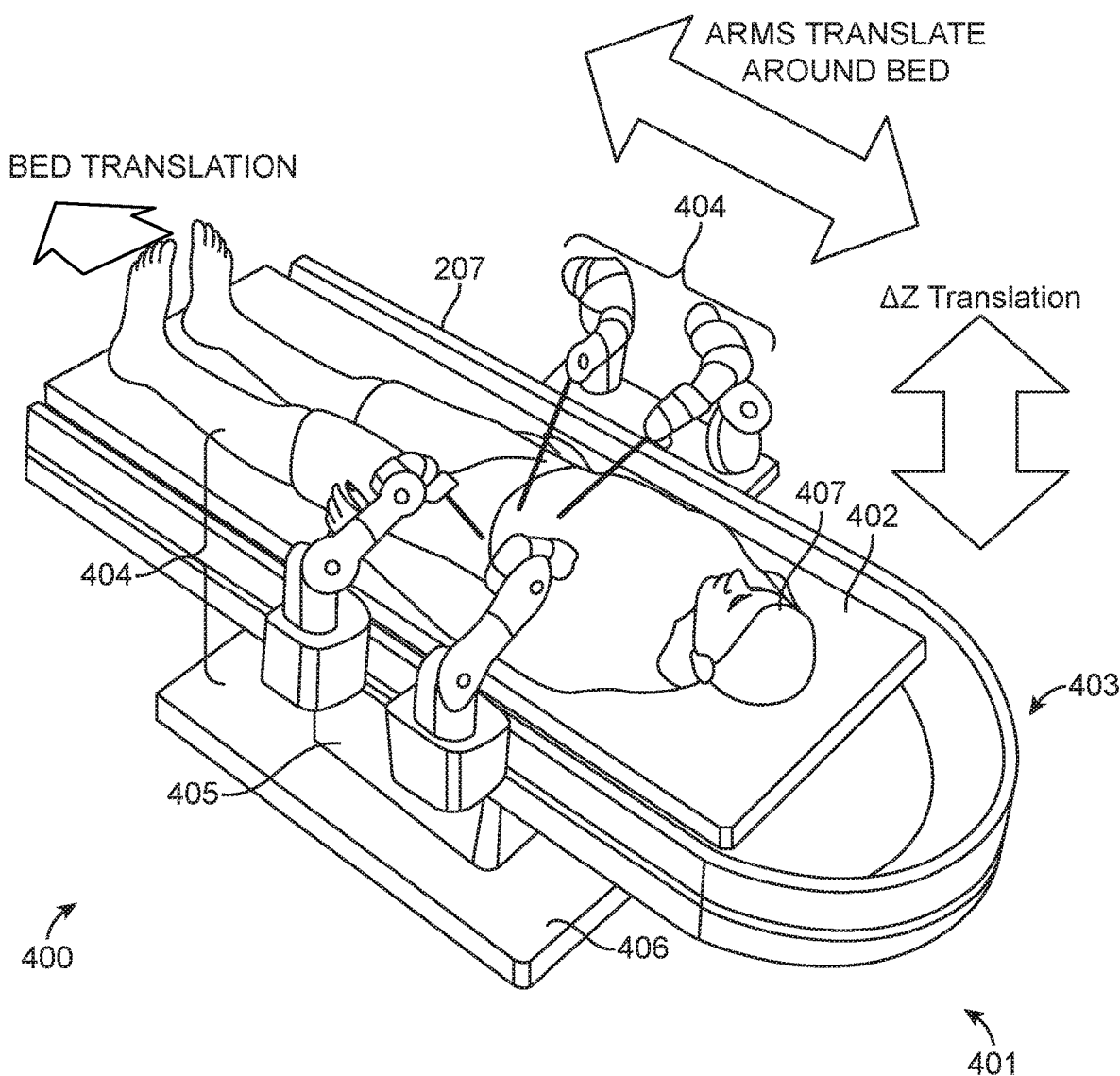
FIG. 4 illustrates a surgical bed with a rounded track for robotic arms along the edge of the bed, consistent with an embodiment of the present invention.

FIG. 4 illustrates a surgical bed with a rounded track for robotic arms along the edge of the bed, consistent with an embodiment of the present invention. As shown in the isometric view 400 of the robotic system 401, the system 401 comprises of a surgical bed 402, a rail 403 (or "track") for mechanical arms 404, a support stand 405, and a system base 406. The surgical bed 402 may be configured to translate horizontally to position patient 407 relative to mechanical arms 404.

Encircling the surgical bed 402, the rail 403 provides a structure to slidingly translate the mechanical arms 404 to a desired location around the surgical bed 402. The rail 403, which may be referred to as a "track", and the mechanical arms 404 may be slidingly translated along it in order to facilitate access for the arms. The rail 403 also provides allows for the conveyance and reception of power, controls, fluidics, aspiration to the mechanical arms 404.

The mechanical arms 404 may be operatively coupled to the rail 403. The mechanical arms 404 may also be robotic. The translation of the mechanical arms 404 may be actuated either manually or robotically. The mechanical arms 404 may be coupled independently to the rail 403 or in groups via a mechanical carriage that may slide around the rail 403. In addition to providing structural support to the mechanical arms 404, the carriage may be used to convey and receive power, controls, fluidics, and aspiration to and from the arms 404 to the rail 403. The ability to translate the arms 404 and translate the bed 402 allows for nearly unlimited access to different portions of the anatomy of patient 407.

In combination or individually, the support stand 405 and the system base 406 may be used to house electronics, fluidics, pneumatics, and aspiration. The electronics may be used from control, localization, navigation of the arms 404. Thus, as a robotically-driven platform, system 401 provides for a comprehensive surgical bed and tool solution that may be used to perform any number of procedures around a patient. The support stand 405 may also translate vertically, allowing for easier access to the patient 407 and operative site.

As deployed in view 400, mechanical arms 404 may be positioned to access the abdomen of patient 407 for laparoscopic procedures.

Figure 5A:
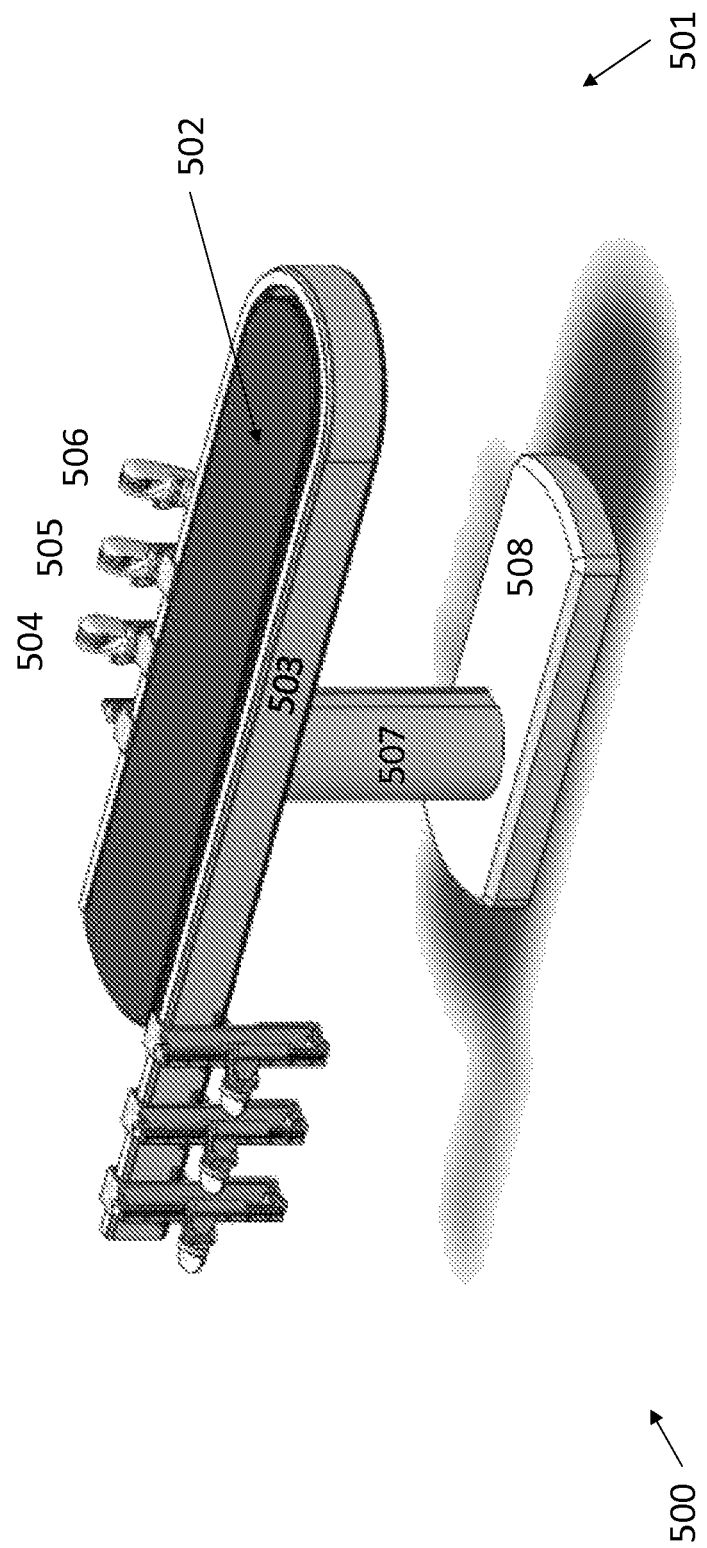
FIG. 5A illustrates a surgical bed with a rounded track for robotic arms along the edge of the bed, consistent with an embodiment of the present invention.

FIG. 5A illustrates a surgical bed with a rounded track for robotic arms along the edge of the bed, consistent with an embodiment of the present invention. As shown in the isometric view 500 of the robotic system 501, the system 501 comprises of a surgical bed 502, a rail 503 (or "track") for mechanical arms 504, 505, 506, a support stand 507, and a system base 508. The surgical bed 502 may be configured to translate horizontally to position a patient relative to mechanical arms 504, 505, 506.

Encircling the surgical bed 502, the rail 503 provides a structure to slidingly translate the mechanical arms 504, 505, 506 to a desired location around the surgical bed 502. The rail 503, which may be referred to as a "track", and the mechanical arms 504, 505, 506 may be slidingly translated along it in order to facilitate access for the arms 504, 505, 506. The rail 503 also provides allows for the conveyance and reception of power, controls, fluidics, aspiration to the mechanical arms 504, 505, 506.

The mechanical arms 504, 505, 506 may be operatively coupled to the rail 503. The mechanical arms 504, 505, 506 may also be robotic. The translation of the mechanical arms 504, 505, 506 may be actuated either manually or robotically. The mechanical arms 504, 505, 506 may be coupled independently to the rail 503 or individually or in groups via mechanical carriages that may slide around the rail 503. In addition to providing structural support to the mechanical arms 504, 505, 506 a carriage may be used to convey and receive power, controls, fluidics, and aspiration to and from the arms 504, 505, 506 to the rail 503. The ability to translate the arms 504, 505, 506 and translate the bed 502 allows for nearly unlimited access to different portions of the anatomy of a patient.

In combination or individually, the support stand 507 and the system base 508 may be used to house electronics, fluidics, pneumatics, and aspiration. The electronics may be used from control, localization, navigation of the arms 504, 505, 506. Thus, as a robotically-driven platform, system 501 provides for a comprehensive surgical bed and tool solution that may be used to perform any number of procedures around a patient. The support stand 507 may also translate vertically, allowing for easier access to the patient and operative site.

As deployed in view 500, mechanical arms 504, 505, 506 may be positioned to access the abdomen of patient for laparoscopic procedures, while the carriages on the other side of rail 503 may be positioned to hold mechanical arms to create a virtual rail for access points in the lower abdomen (e.g., urology, ureteroscopy, or hysteroscopy).

Figure 5B:
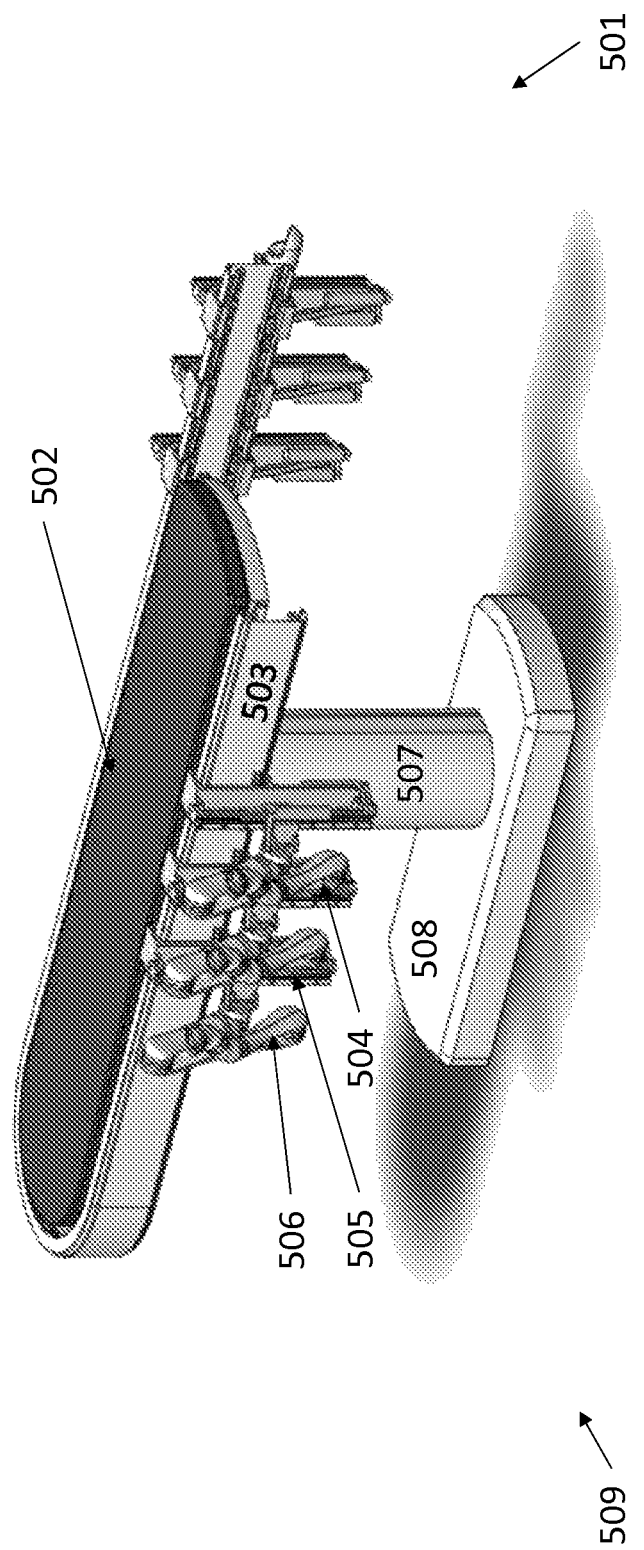
FIG. 5B illustrates the surgical bed with a rounded track from FIG. 5A, consistent with an embodiment of the present invention.

FIG. 5B illustrates the surgical bed with a rounded track from FIG. 5A, consistent with an embodiment of the present invention. Reverse isometric view 509 provides a different perspective of the robotic system 501, surgical bed 502, rail 503 (or "track") for mechanical arms 504, 505, 506 a support stand 507, and a system base 508.

Figure 5C:
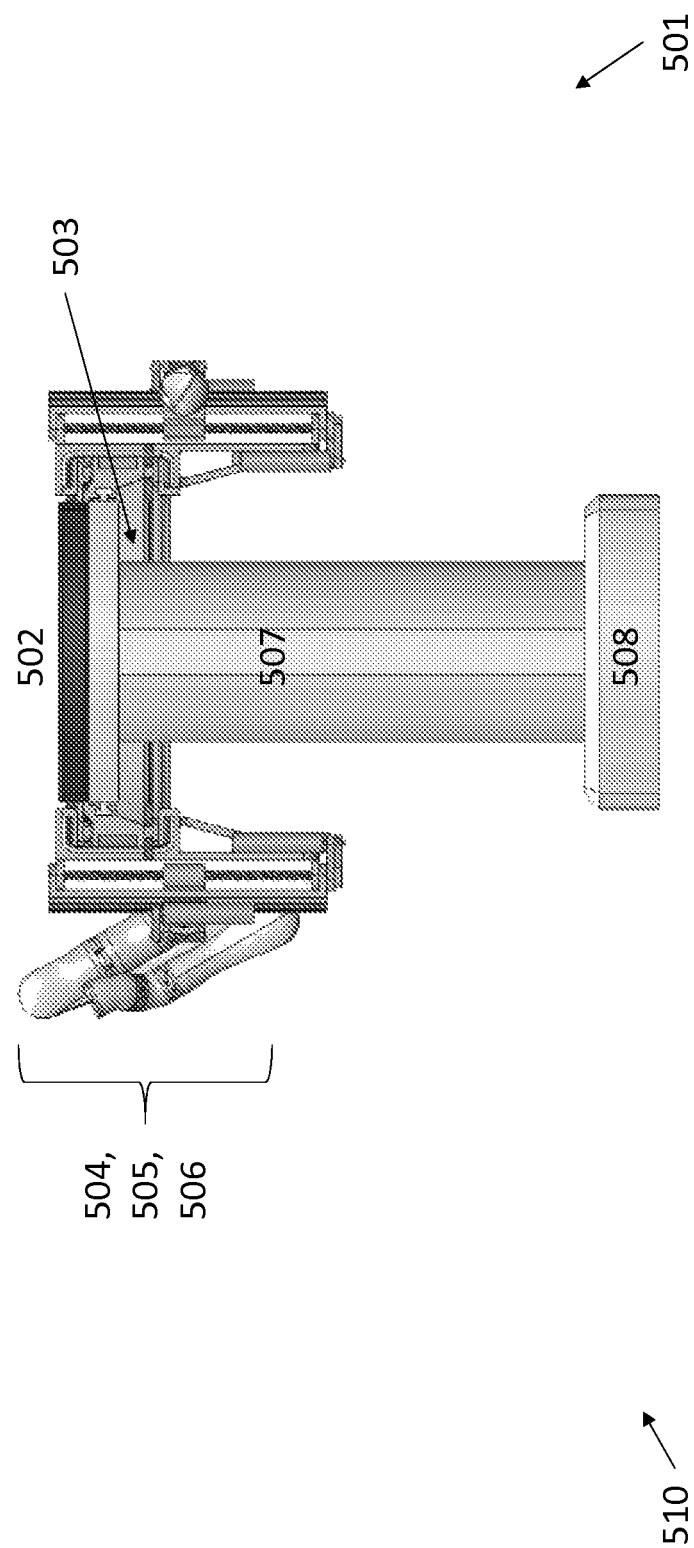
FIG. 5C illustrates the surgical bed with a rounded track from FIGS. 5A, 5B, consistent with an embodiment of the present invention.

FIG. 5C illustrates the surgical bed with a rounded track from FIGS. 5A, 5B, consistent with an embodiment of the present invention. Rear view 510 provides a different perspective of the robotic system 501, surgical bed 502, rail 503 (or "track") for mechanical arms 504, 505, 506, support stand 507, and a system base 508.

Figure 5D:
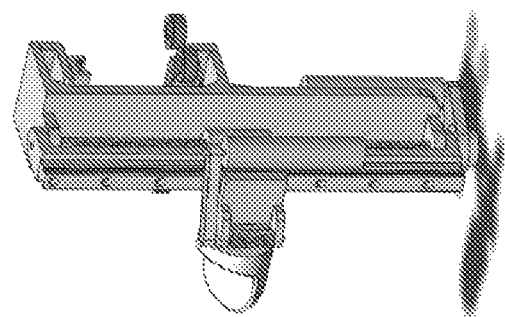
FIG. 5D illustrates several views of carriages for mechanical arms used in system 501 from FIGS. 5A, 5B.
Figure 5D:
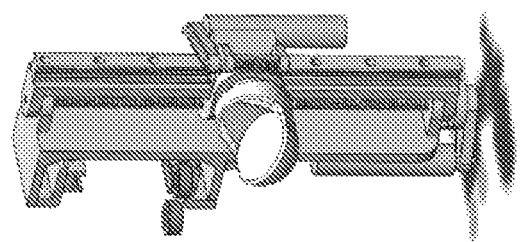
Figure 5D:
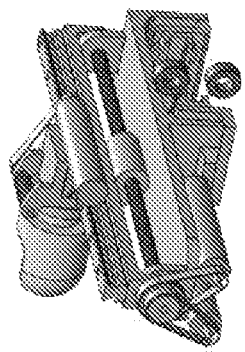

FIG. 5D illustrates several views of carriages for mechanical arms used in system 501 from FIGS. 5A, 5B, 5C, consistent with an embodiment of the present invention. Side views 511, 512, 513 provide different perspectives on a mechanically-driven carriage in system 501.

Figure 5E:
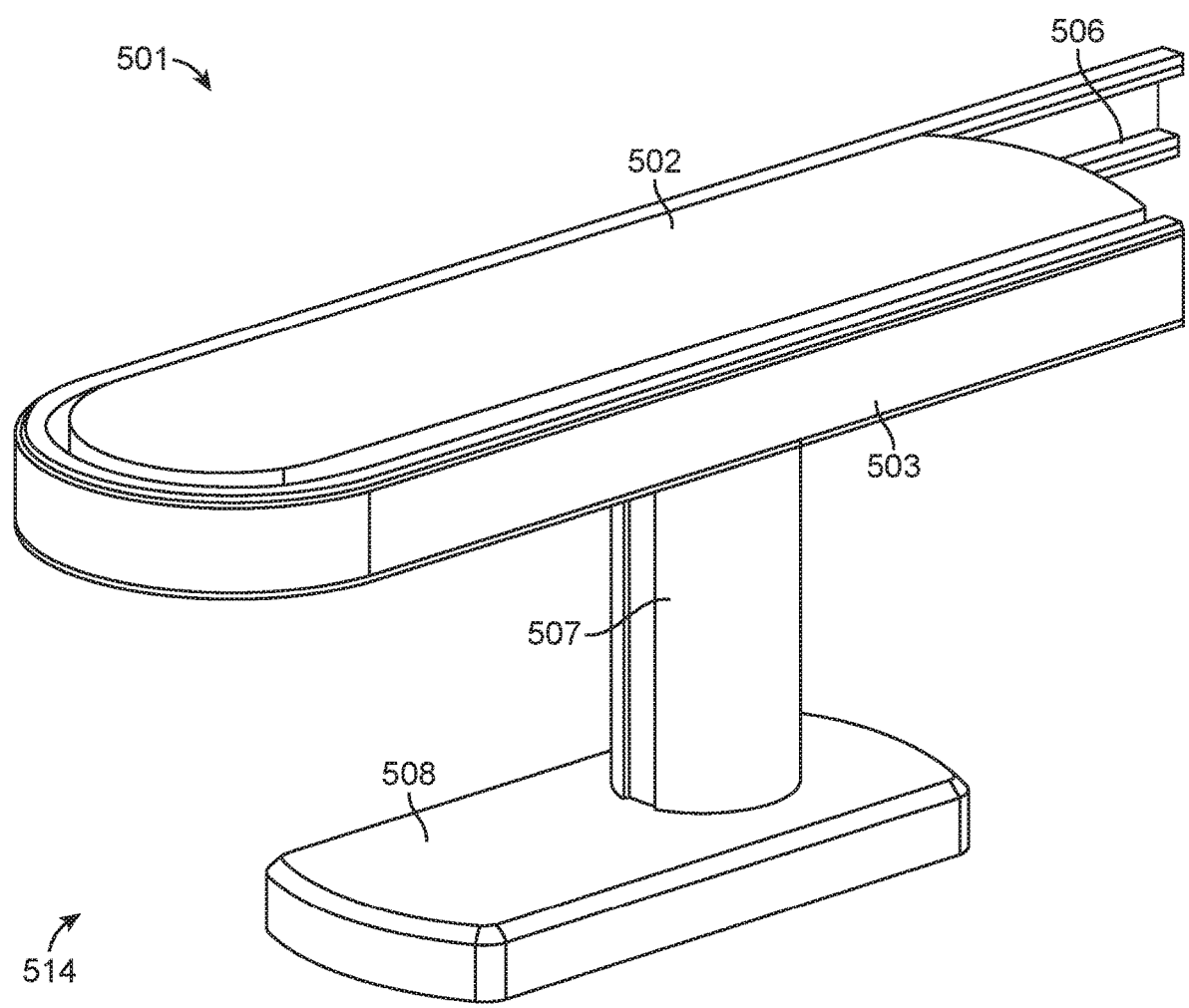
FIG. 5E illustrates the surgical bed with a rounded track from FIG. 5A, consistent with an embodiment of the present invention.

FIG. 5E illustrates the surgical bed with a rounded track from FIG. 5A, consistent with an embodiment of the present invention. View 514 provides a different perspective of the robotic system 501, surgical bed 502, rail 503 (or "track"), support stand 507, and system base 508, absent mechanical arms 504, 505, 506.

Figure 6A:
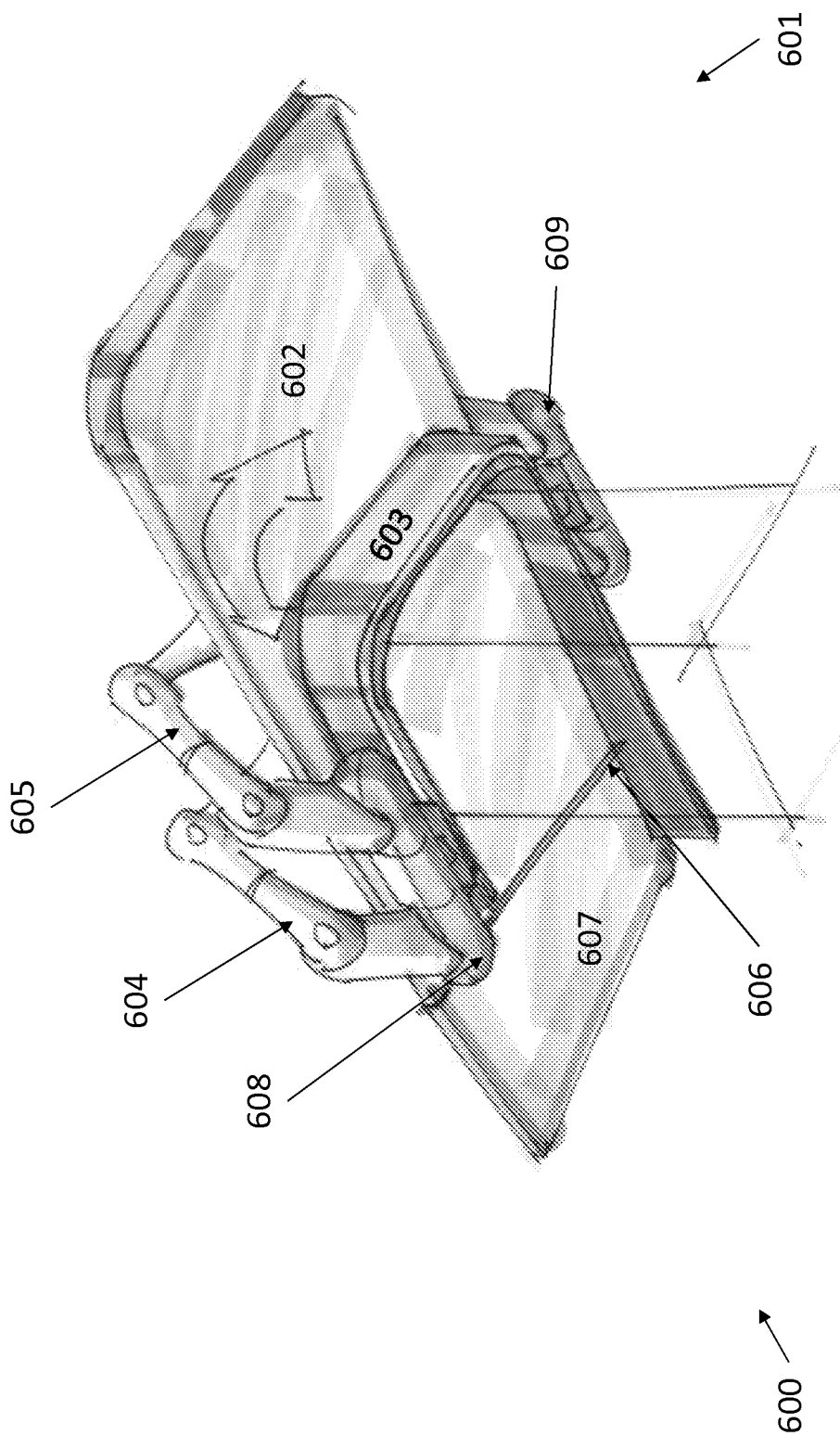
FIGS. 6A and 6B illustrate a surgical bed with a rounded track for robotic arms along the edge of the bed, consistent with an embodiment of the present invention.

FIG. 6A illustrates a surgical bed with a rounded track for robotic arms along the edge of the bed, consistent with an embodiment of the present invention. As shown in the view 600, the system 601 comprises of a surgical bed 602, a rail 603 (or "track") for mechanical arms 604, 605. The surgical bed 602 may be configured to translate horizontally to position a patient relative to mechanical arms 604, 605. The surgical bed 602 allows for a hinge 606 such that a portion 607 of surgical bed 602 may be declined at a different angle from the rest of the bed 602. As discussed earlier, this may be desirable for certain operations, such as when performing a procedure that requires access a patient's lower abdomen, such as ureteroscopy, hysteroscopy, or colonoscopy.

Underneath the surgical bed 602, the rail 603 provides a structure to slidingly translate the mechanical arms 604, 605 to a desired location around the surgical bed 602. The rail 603, which may be referred to as a "track", and the mechanical arms 604, 605 may be slidingly translated along it in order to facilitate access for the arms 604, 605. The rail 603 also provides allows for the conveyance and reception of power, controls, fluidics, aspiration to the mechanical arms 604, 605. As shown in FIG. 6A, there may be a shorter leg and longer leg portion of the U-shape rail 603. In some embodiments, the rail 603 may be fully circular, rather than a U-shaped.

The mechanical arms 604, 605 may be operatively coupled to the rail 603. The mechanical arms 604, 605 may also be robotic. The translation of the mechanical arms 604, 605 may be actuated either manually or robotically. The mechanical arms 604, 605 may be coupled independently to the rail 603 or individually or in groups (as shown) via a mechanical carriage 608 that may slide around the rail 603. In addition to providing structural support to the mechanical arms 604, 605, the carriage 606 may be used to convey and receive power, controls, fluidics, and aspiration to and from the arms 604, 605 to the rail 603. The ability to translate the arms 604, 605 and translate the bed 602 allows for nearly unlimited access to different portions of the anatomy of a patient.

Not shown, system 601 may also incorporate a support stand and the system base to house electronics, fluidics, pneumatics, and aspiration. The electronics may be used from control, localization, navigation of the arms 604, 605. Thus, as a robotically-driven platform, system 601 provides for a comprehensive surgical bed and tool solution that may be used to perform any number of procedures around a patient. The support stand may also translate vertically, allowing for easier access to the patient and operative site. The support stand may also support vertical translation of the rail 603 in order to facilitate access to particular anatomical access points.

As deployed in view 600, mechanical arms 604, 605 on carriage 608 may be positioned to access the abdomen of patient for procedures, such as laparoscopy or endoscopy, while a carriage 609 on the other side of rail 603 may be positioned to hold additional mechanical arms.

Figure 6B:
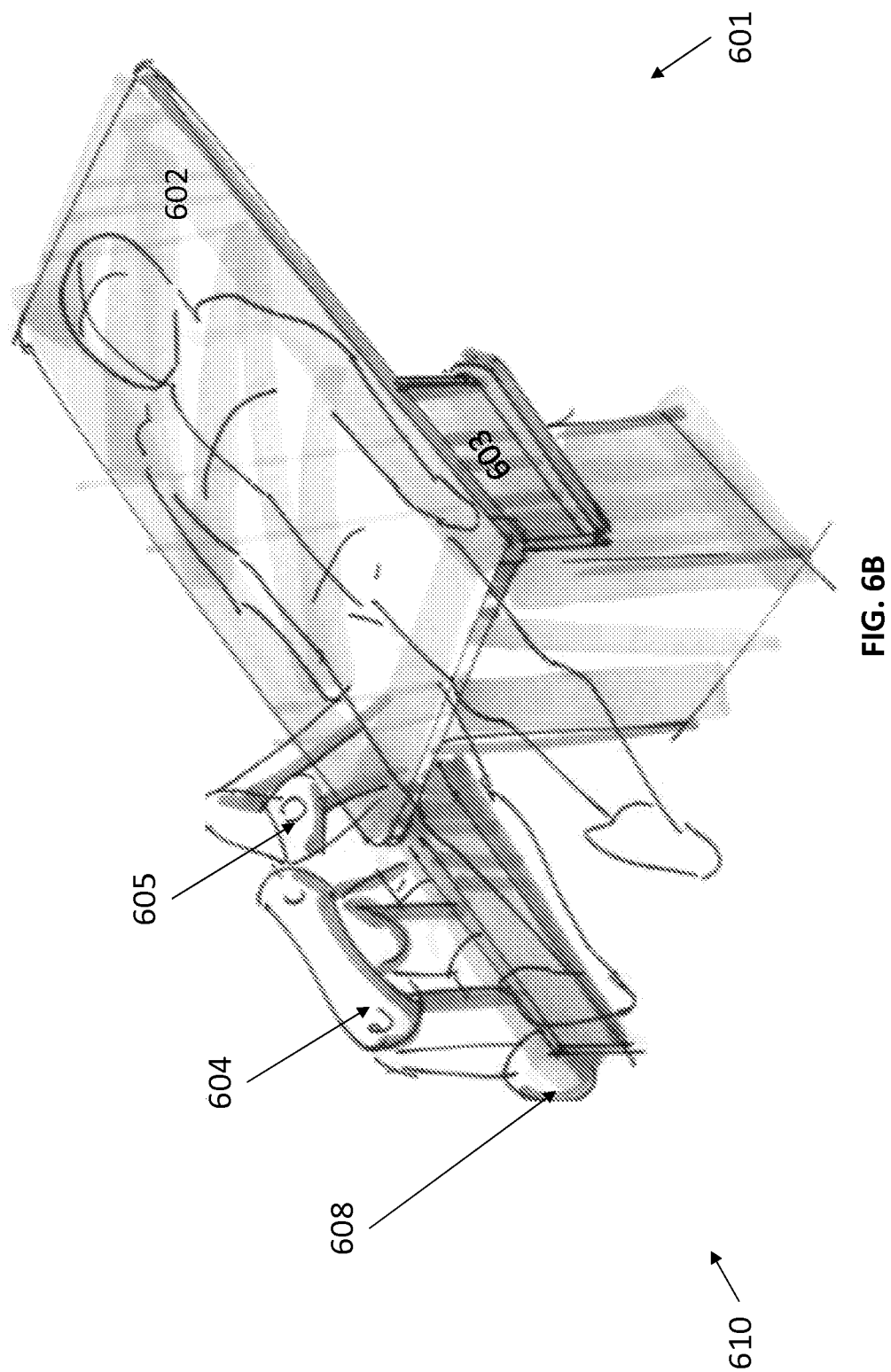

FIG. 6B illustrates the surgical bed with a rounded track from FIG. 6A. As shown in the view 610, mechanical arms 604, 605 on carriage 608 may be slidingly translated to the long side of the rail 603. View 610 also provides a view of a support base. As deployed in view 610, mechanical arms 604, 605 on carriage 608 may be positioned to form a virtual rail for access to the anatomical lumens in the lower abdomen for various procedures, such as ureteroscopy, hysteroscopy, or colonoscopy. To facilitate access surgical bed 602 has been slidingly translated forwards from the rail 603.

Figure 7A:
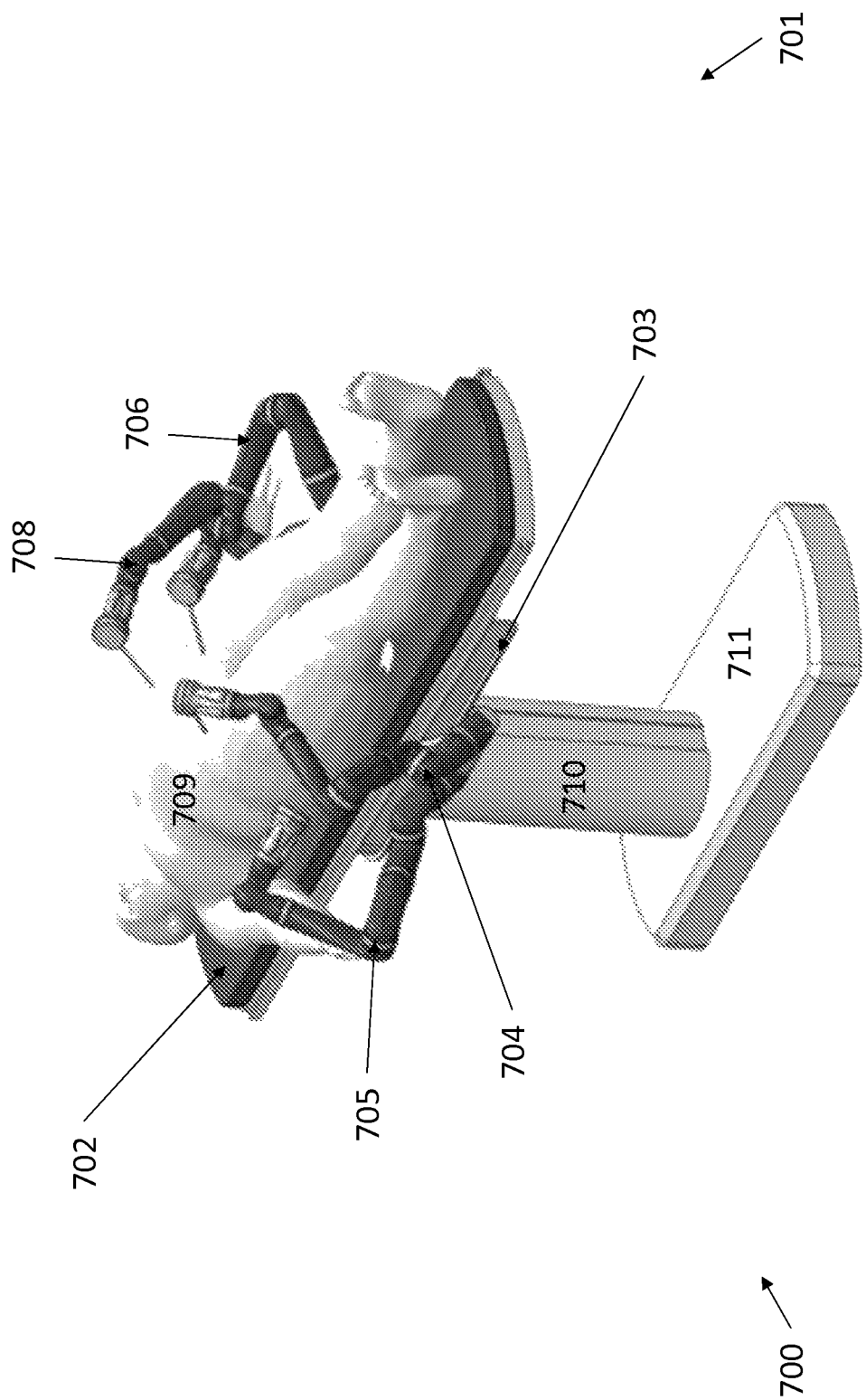
FIG. 7A illustrates a surgical bed with a rounded track for robotic arms underneath the edge of the bed, consistent with an embodiment of the present invention.

FIG. 7A illustrates a surgical bed with a rounded track for robotic arms underneath the edge of the bed, consistent with an embodiment of the present invention. As shown in the view 700, the system 701 comprises of a surgical bed 702, a rail 703 (or "track") for mechanical arms 704, 705, 706, 708. The surgical bed 702 may be configured to translate horizontally to position patient 709 relative to mechanical arms 704, 705, 706, 708. The surgical bed 702 may include a hinge such that the lower portion of surgical bed 702 may be declined at a different angle from the rest of the bed 702. As discussed earlier, this may be desirable for certain operations, such as when performing a procedure that requires access a patient's lower abdomen, such as ureteroscopy, hysteroscopy, or colonoscopy.

Underneath the surgical bed 702, the rail 703 provides a structure to slidingly translate the mechanical arms 704, 705, 706, 708 to a desired location around the surgical bed 702. The rail 703, which may be referred to as a "track" and the mechanical arms 704, 705 may be slidingly translated along it in order to facilitate access for the arms 704, 705, 706, 708. The rail 703 also provides allows for the conveyance and reception of power, controls, fluidics, aspiration to the mechanical arms 704, 705, 706, 708.

The mechanical arms 704, 705, 706, 708 may be operatively coupled to the rail 703. The mechanical arms 704, 705, 706, 708 may also be robotic. The translation of the mechanical arms 704, 705, 706, 708 may be actuated either manually or robotically. The mechanical arms 704, 705, 706, 708 may be coupled independently to the rail 703 or individually or in groups via a mechanical carriage that may slide around the rail 703. In addition to providing structural support to the mechanical arms 704, 705, 706, 708, the carriage may be used to convey and receive power, controls, fluidics, and aspiration to and from the arms 704, 705, 706, 708 to the rail 703. The ability to translate the arms 704, 705, 706, 708 and translate the bed 702 allows for nearly unlimited access to different portions of the anatomy of a patient.

System 701 may also incorporate support stand 710 and system base 711 to house electronics, fluidics, pneumatics, and aspiration. The electronics may be used from control, localization, navigation of the arms 704, 705, 706, 708. Thus, as a robotically-driven platform, system 701 provides for a comprehensive surgical bed and tool solution that may be used to perform any number of procedures around a patient. The rail 703 on support stand 710 may also translate vertically, allowing for easier access to the patient and operative site. The support stand may also telescope.

As deployed in view 700, mechanical arms 704, 705, 706, 708 may be positioned to access the abdomen of patient 709 for laparoscopic procedures, using a variety of rigid or semi-rigid laparoscopic instruments.

Figure 7B:
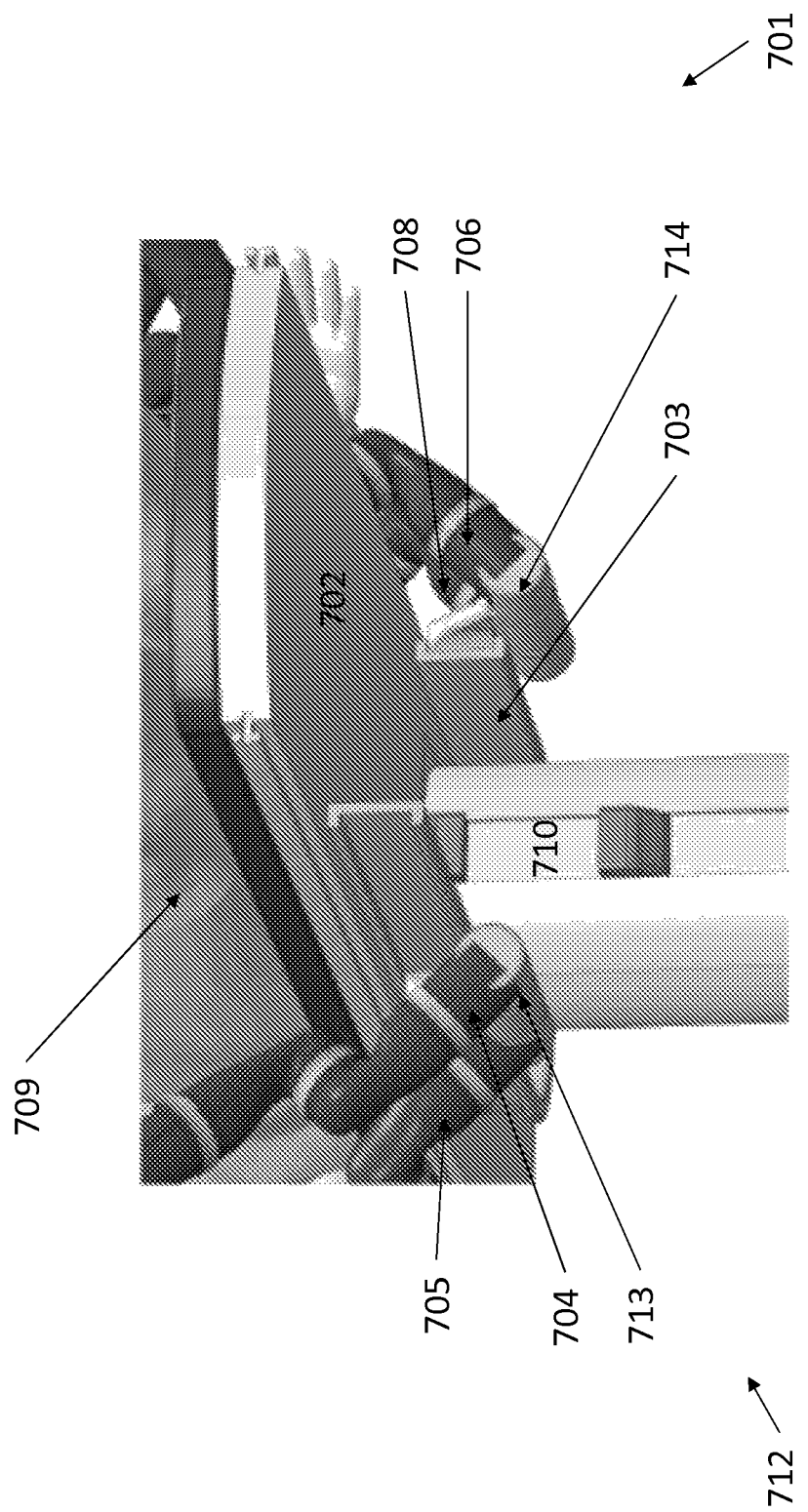
FIG. 7B illustrates the underside of the surgical bed with a rounded track from FIG. 7A.

FIG. 7B illustrates the underside of the surgical bed with a rounded track from FIG. 7A. As shown in the view 712, mechanical arms 704, 705, 706, 708 may be coupled to the rail 703 using carriages 713 and 714, which may be slidingly translated along rail 703. Carriages 713 and 714 may be oriented at various angles from rail 703 to provide an additional access to the patient 709. View 712 also provides a view of a support base 709 which shows structures to vertically translate rail 703 and bed 702.

Figure 7C:
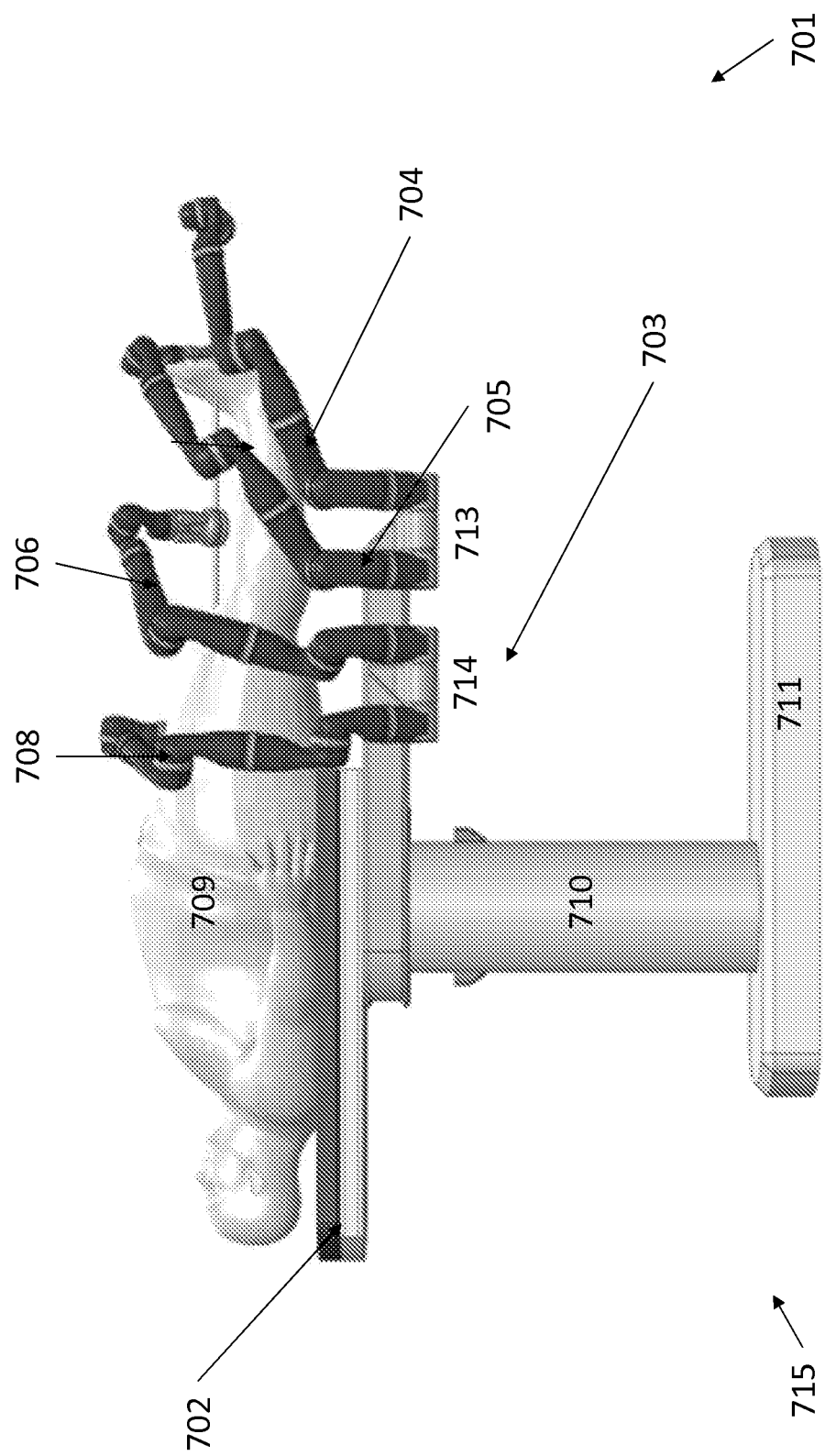
FIG. 7C illustrates the surgical bed with a rounded track from FIGS. 7A, 7B.

FIG. 7C illustrates the surgical bed with a rounded track from FIGS. 7A, 7B. As shown in side view 715, carriages 713 and 714 may be positioned along rail 703 such that mechanical arms 704, 705, 706, 708 may be arranged to form a virtual rail to guide an endoscopic device 716 into an anatomical lumen in the lower abdomen of patient 709 for a procedure such as ureteroscopy, hysteroscopy, or colonoscopy.

Figure 7D:
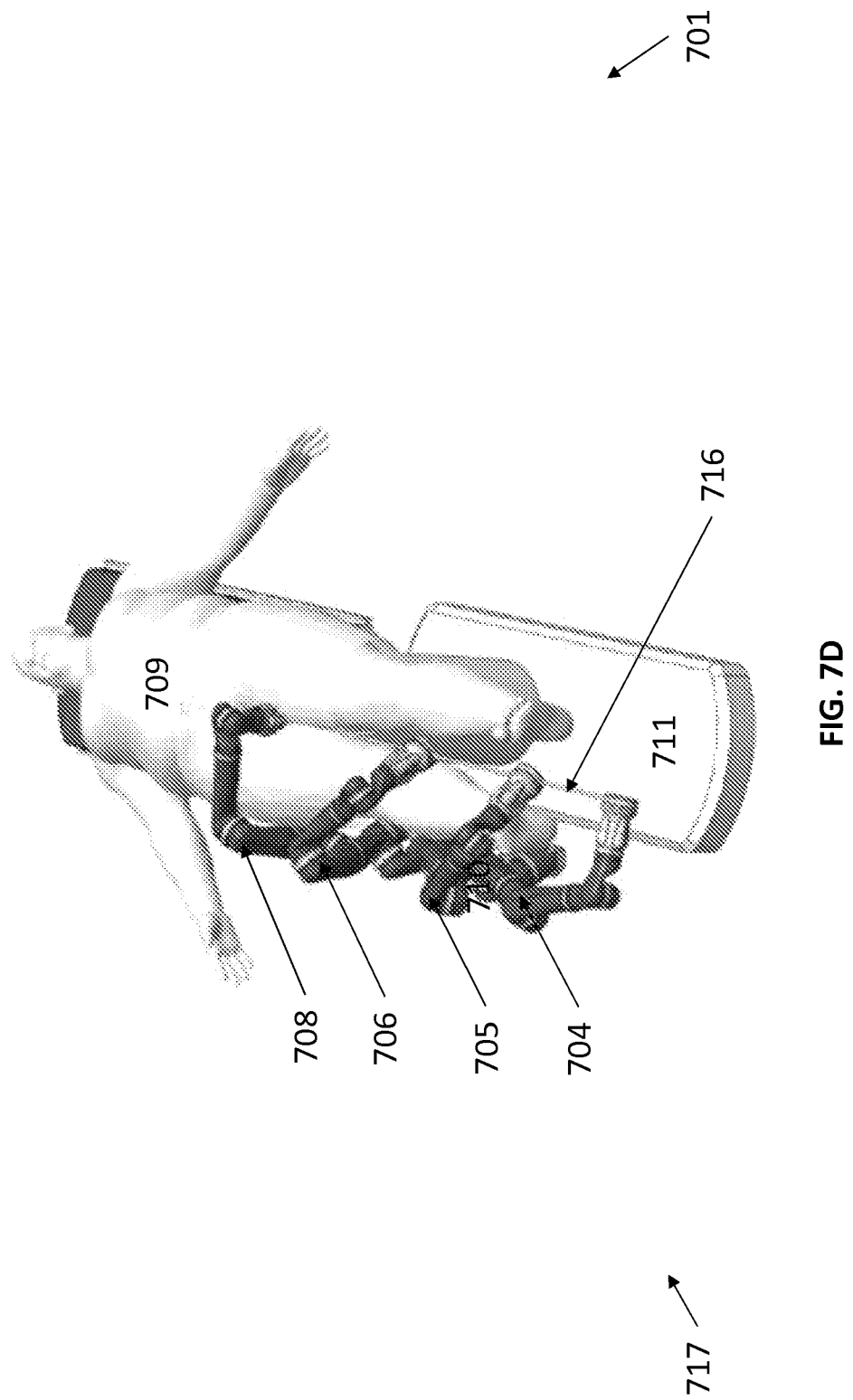
FIG. 7D illustrates the surgical bed with a rounded track from FIGS. 7A, 7B, 7C.

FIG. 7D illustrates the surgical bed with a rounded track from FIGS. 7A, 7B, 7C. Top view 717 provides a different perspective of the positioning of mechanical arms 704, 705, 706, 708 to form a virtual rail to guide an endoscopic device 716 into an anatomical lumen in the lower abdomen of patient 709 for a procedure such as ureteroscopy, hysteroscopy, or colonoscopy.

Figure 7E:
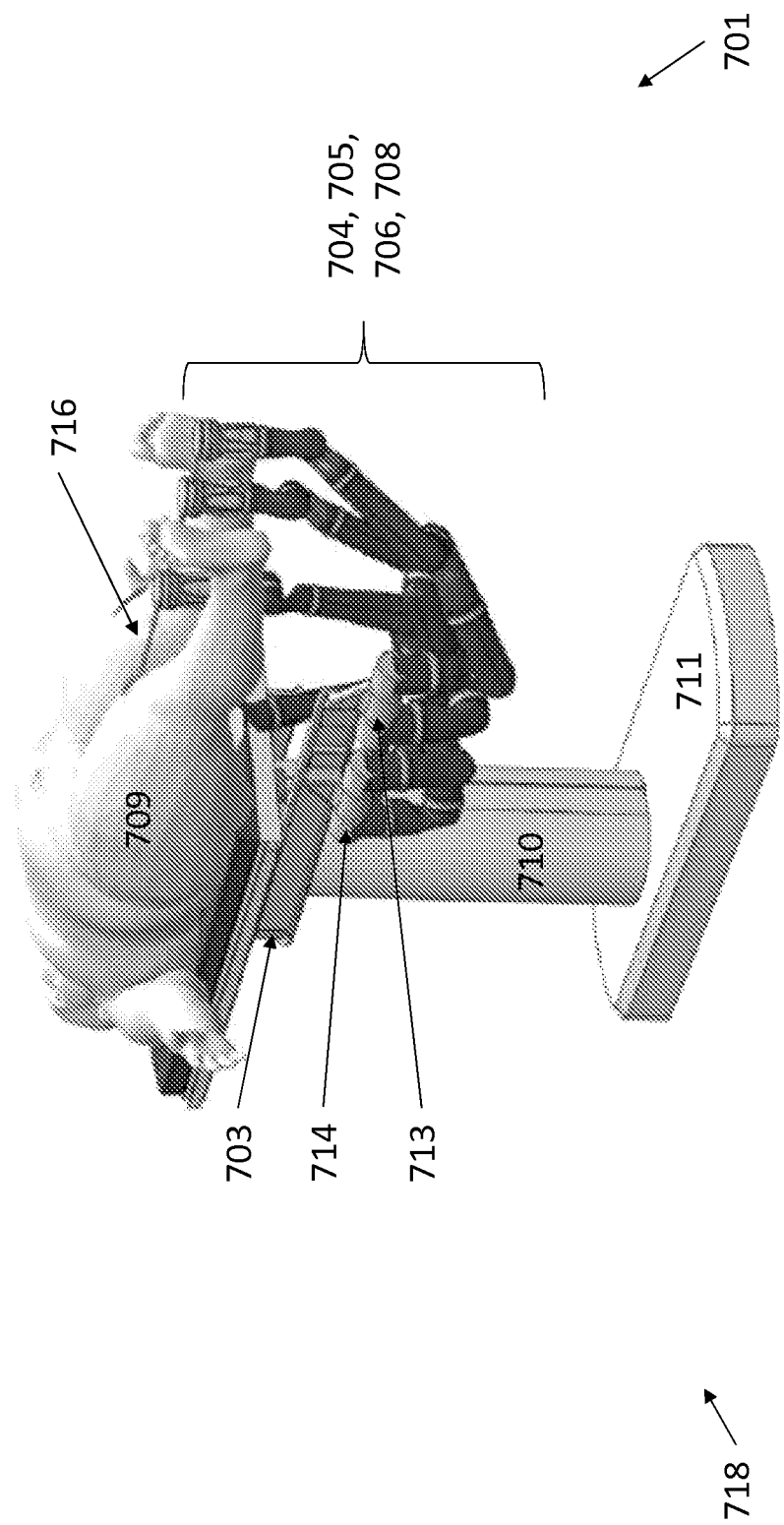
FIG. 7E illustrates the surgical bed with a rounded track from FIG. 7C.

FIG. 7E illustrates the surgical bed with a rounded track from FIG. 7C. Isometric view 718 provides an alternative positioning of mechanical arms 704, 705, 706, 708 to form a virtual rail to guide an endoscopic device 714 into an anatomical lumen in the lower abdomen of patient 709 for a procedure such as ureteroscopy, hysteroscopy, or colonoscopy. In view 717, the carriages 713 and 714 may be oriented below rail 703 to position mechanical arms 704, 705, 706, 708 such that the virtual rail is positioned lower than shown in FIGS. 7C and 7D.

Figure 7F:
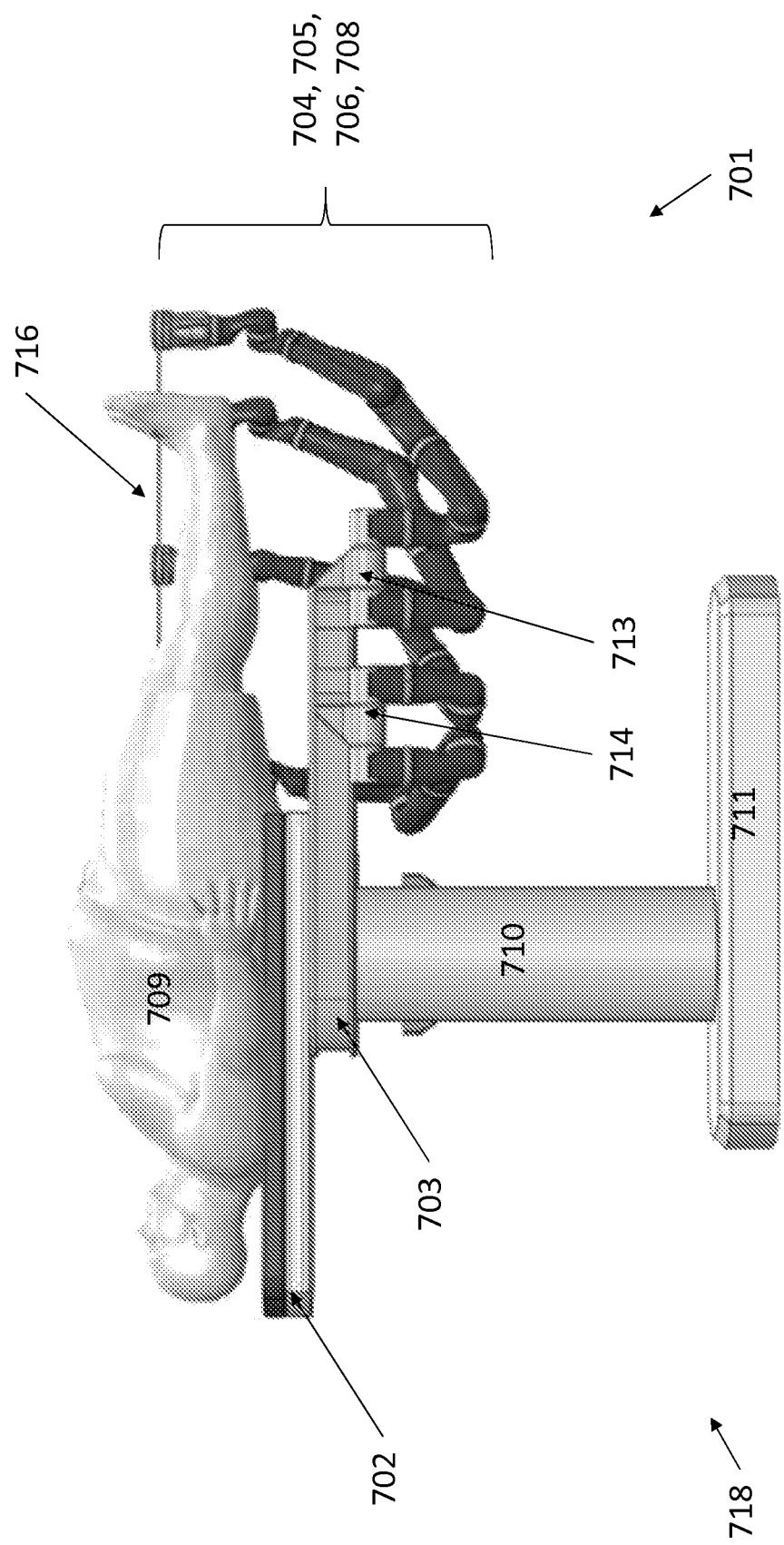
FIG. 7F illustrates the surgical bed with a rounded track from FIG. 7E.

FIG. 7F illustrates the surgical bed with a rounded track from FIG. 7E. Side view 719 provides a different perspective of the positioning of carriages 713 and 714 such that mechanical arms 704, 705, 706, 708 form a virtual rail to guide an endoscopic device 716 into an anatomical lumen in the lower abdomen of patient 709 for a procedure such as ureteroscopy, hysteroscopy, or colonoscopy.

Figure 7G:
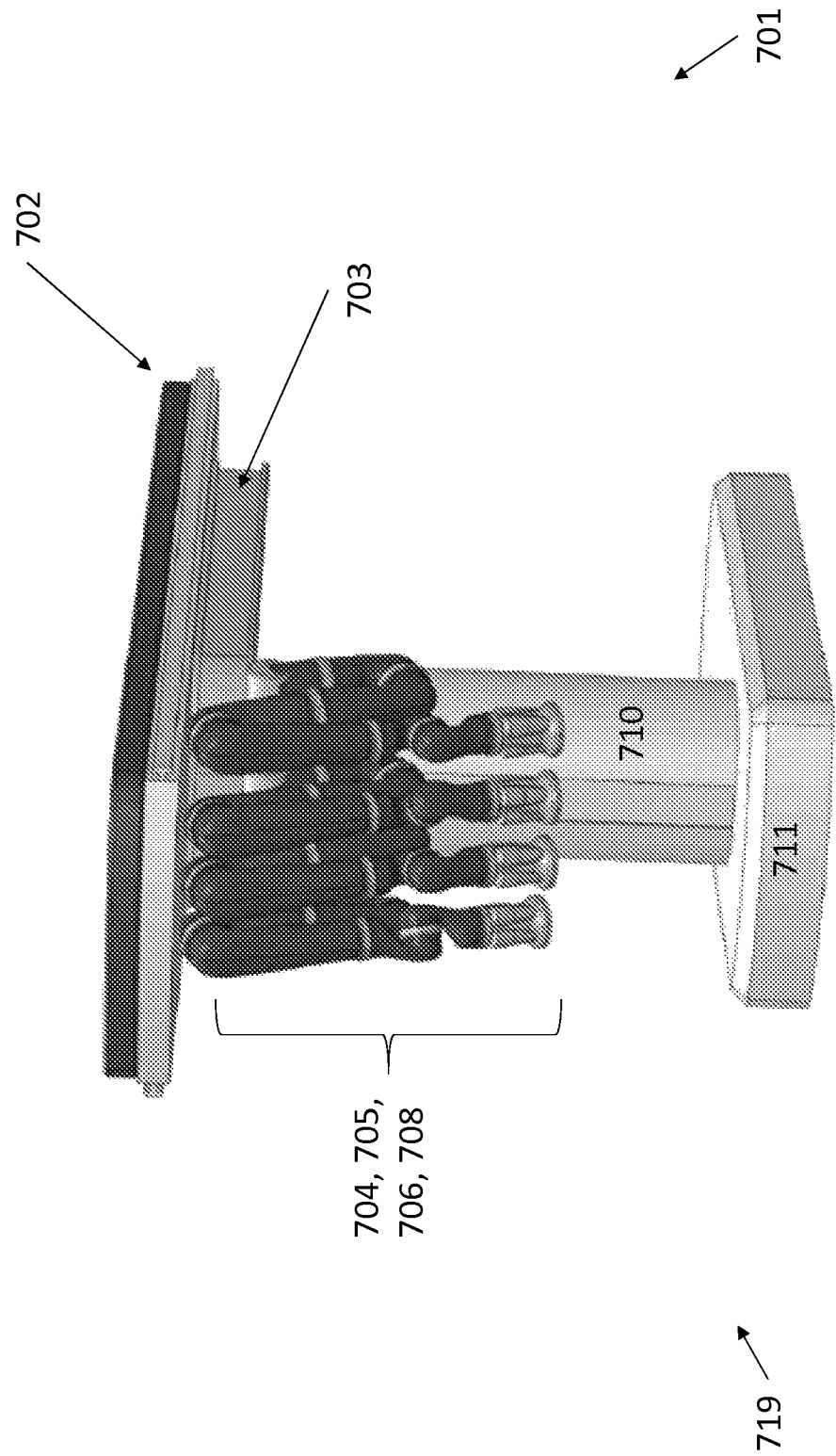
FIG. 7G illustrates the surgical bed with a rounded track from FIGS. 7A-7F.

FIG. 7G illustrates the surgical bed with a rounded track from FIGS. 7A-7F. View 719 shows stowage of mechanical arms 704, 705, 706, 708 through positioning of carriages 713 and 714 together along rail 703 under surgical bed 702.

Figure 8A:
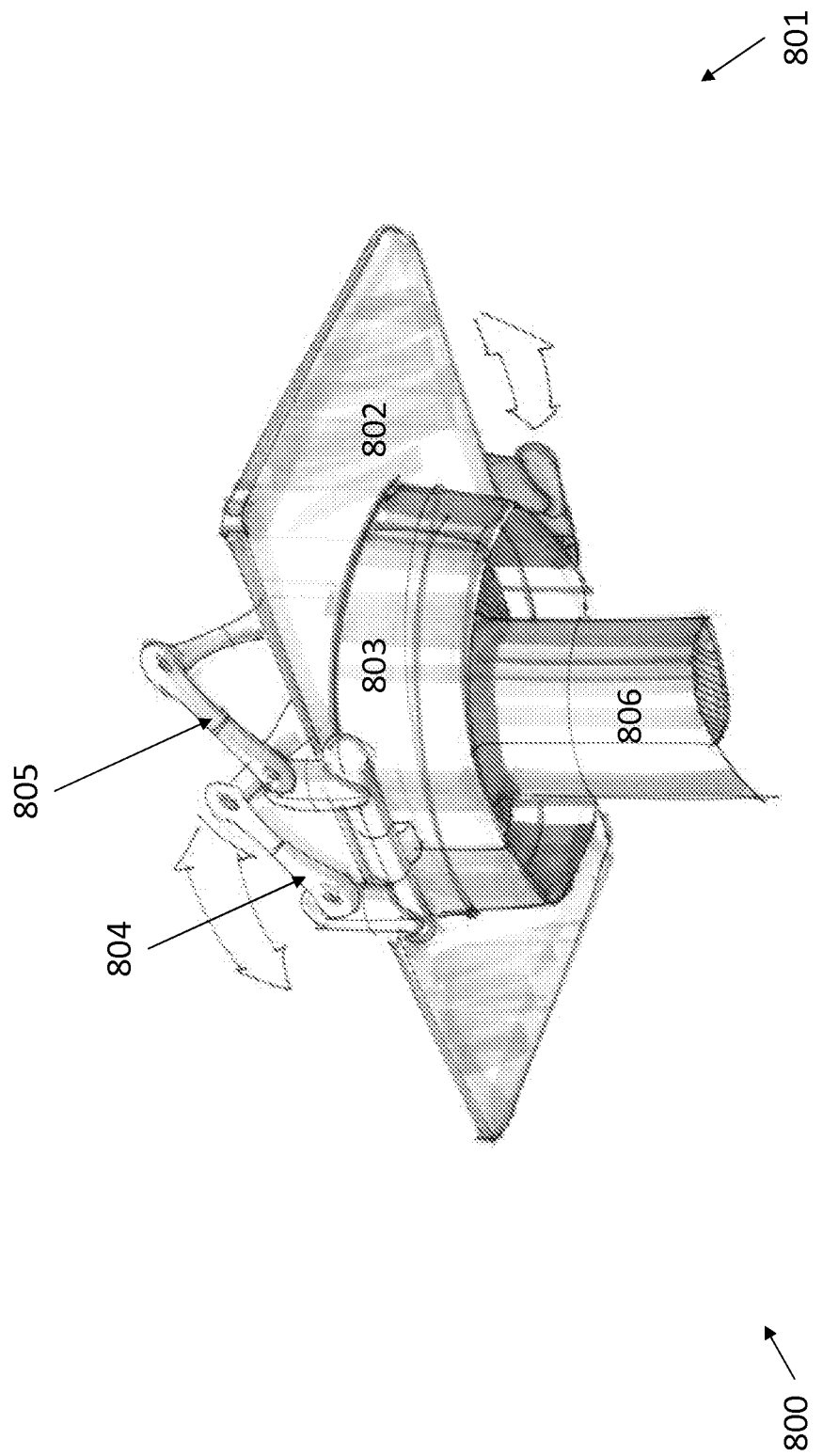
FIGS. 8A and 8B illustrate a surgical bed with a rounded track for robotic arms underneath the edge of the bed, consistent with an embodiment of the present invention.
Figure 8B:
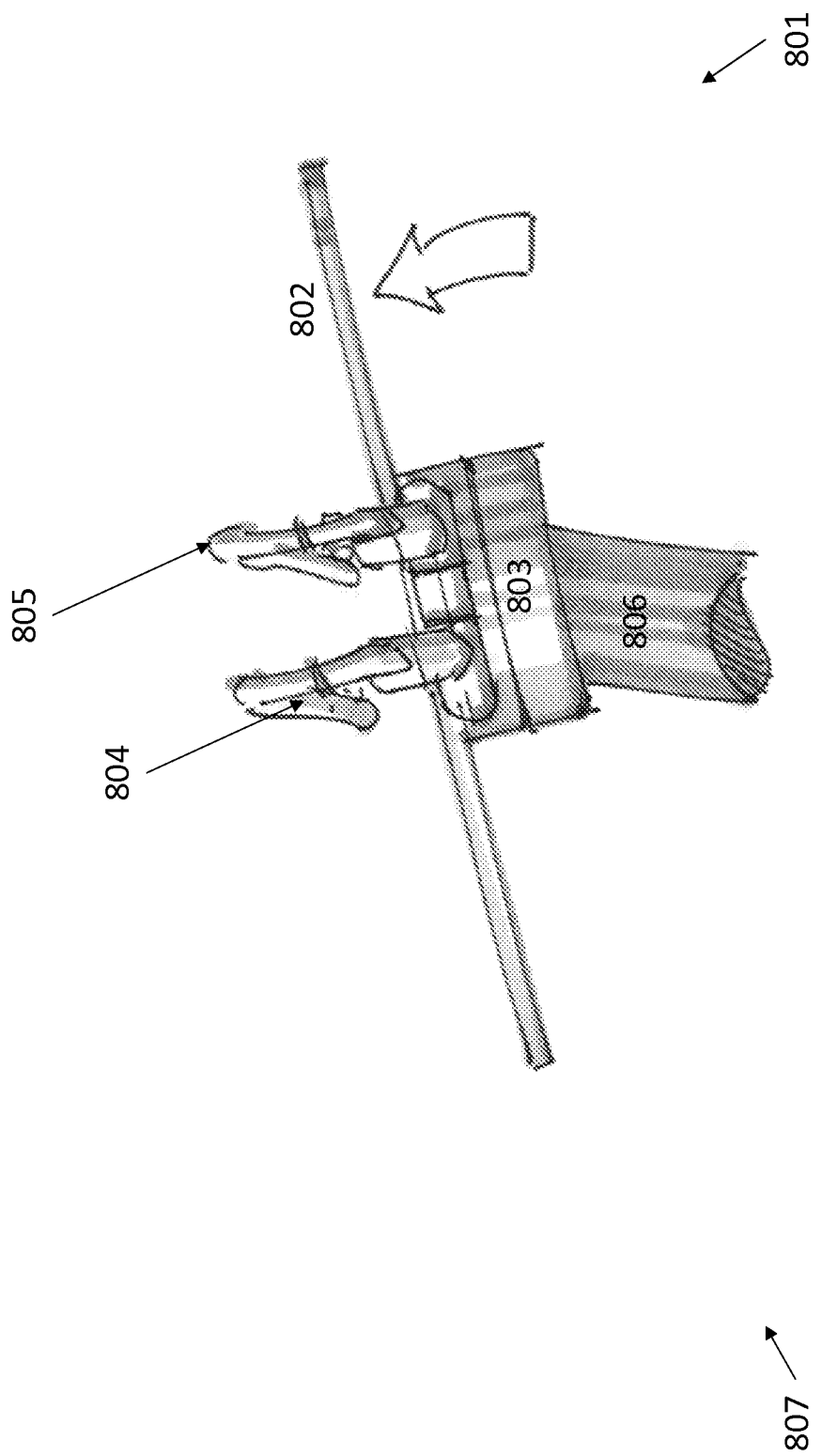

FIGS. 8A and 8B illustrate a surgical bed with a rounded track for robotic arms underneath the edge of the bed, consistent with an embodiment of the present invention. As shown in the view 800, the system 801 comprises of a surgical bed 802, a rail 803 (or "track") for mechanical arms, such as 804, 805. The surgical bed 802 may be configured to translate horizontally to position a patient relative to the mechanical arms. As shown in view 807 from FIG. 8B, the surgical bed 802 may tilted on the support stand 806 to improve physician access to the patient.

Underneath the surgical bed 802, the rail 803 provides a structure to slidingly translate the mechanical arms 804, 805 to a desired location around the surgical bed 802. The rail 803, which may be referred to as a "track", and the mechanical arms 804, 805 may be slidingly translated along it in order to facilitate access for the arms. The rail 803 also provides allows for the conveyance and reception of power, controls, fluidics, aspiration to the mechanical arms.

The mechanical arms may be operatively coupled to the rail 803. The mechanical arms may also be robotic. The translation of the mechanical arms 804, 805 may be actuated either manually or robotically. The mechanical arms 804, 805 may be coupled independently to the rail 803 or individually or in groups via a mechanical carriage that may slide around the rail 803. In addition to providing structural support to the mechanical arms 804, 805 the carriage may be used to convey and receive power, controls, fluidics, aspiration to and from the arms 804, 805 to the support base 806. The ability to translate the arms 804, 805 and translate the bed 802 allows for nearly unlimited access to different portions of the anatomy of a patient.

System 801 may also incorporate support stand 806 to house electronics, fluidics, pneumatics, and aspiration. The electronics may be used from control, localization, navigation of the arms 804, 805. Thus, as a robotically-driven platform, system 801 provides for a comprehensive surgical bed and tool solution that may be used to perform any number of procedures around a patient. The rail 803 on support stand 806 may also translate vertically, allowing for easier access to the patient and operative site. The support stand may also telescope.

As deployed in view 800, mechanical arms 804, 805 may be positioned to access the abdomen of a patient for laparoscopic procedures, using a variety of rigid or semi-rigid laparoscopic instruments.

The aforementioned embodiments of the present invention may be designed to interface with robotics instrument device manipulators, tools, hardware, and software such as those disclosed in the aforementioned patent applications that are incorporated by reference. For example, the embodiments in this specification may be configured to be driven by an instrument drive mechanism or an instrument device manipulator that is attached to the distal end of a robotic arm through a sterile interface, such as a drape. As part of a larger robotics system, robotic control signals may be communicated from a remotely-located user interface, down the robotic arm, and to the instrument device manipulator to control the instrument or tool.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A medical system comprising:
    a base;
    a stand coupled to the base;
    a bed supported by the stand, the bed having a first edge and a second edge, the first edge being longer than the second edge;
    a first rail portion extending along of the first edge of the bed;
    at least one arm attached to the first rail portion; and
    control electronics configured to (i) stow the at least one arm by moving the at least one arm towards the second edge and beneath the bed supported by the stand, wherein the at least one arm is stowed within a perimeter defined by the bed when viewed from above, and (ii) raise the at least one arm over the first edge to perform a medical procedure.

2. The medical system of claim 1, further comprising a second rail portion extending along a length of the bed and at least one arm attached to the second rail portion.

3. The medical system of claim 1, wherein the bed is configured to translate horizontally relative to the first rail portion.

4. The medical system of claim 1, wherein the bed comprises a hinge such that a lower portion of the bed can be declined at a different angle from remaining portions of the bed.

5. The medical system of claim 1, wherein the control electronics are configured to stow the at least one arm by slidingly translating the at least one arm along the first rail portion toward the second edge.

6. The medical system of claim 1, wherein the at least one arm attached to the first rail portion comprises two arms forming a virtual rail to guide an endoscopic device.

7. The medical system of claim 1, further comprising a second rail portion extending along a third edge of the bed opposite the first edge, and at least one arm attached to the second rail portion, wherein the control electronics are further configured to control the at least one arm attached to the first rail portion and the at least one arm attached to the second rail portion to extend upwardly over the opposing first and third edges of the bed to perform the medical procedure.

8. The medical system of claim 1, further comprising:
    a second rail portion extending along a length of the bed; and
    at least two arms attached to the second rail portion.

9. The medical system of claim 1, wherein the at least one arm attached to the first rail portion comprises at least two arms, and wherein the control electronics are configured to stow the at least two arms by moving the at least two arms together towards the second edge and beneath the bed.

10. The medical system of claim 1, wherein the bed has a longitudinal centerline bisecting the second edge, and wherein the control electronics are configured to stow the at least one arm in a position overlapping the longitudinal centerline and between the second edge and the stand.

11. A medical system comprising:
    a base;
    a stand coupled to the base;

a bed supported by the stand, the bed having a substantially rectangular shape defining a longitudinal centerline extending over the stand;

first and second rail portions extending along the bed on opposing sides of the stand;

a first arm attached to the first rail portion;

a second arm attached to the second rail portion; and control electronics configured to (i) stow the first arm and the second arm by moving the first arm and the second arm to positions beneath the bed with the first arm overlapping the longitudinal centerline, wherein the first arm and the second arm are stowed within a perimeter defined by the bed when viewed from above, and (ii) raise the first arm and the second arm over the bed to perform a medical procedure.

12. The medical system of claim 11, wherein the first arm and the second arm are each capable of robotic control.

13. The medical system of claim 11, wherein the first rail portion and the second rail portion are capable of vertical translation.

14. The medical system of claim 11, further comprising:
a third arm attached to the first portion,
wherein the first and third arms form a virtual rail to guide an endoscopic device into an anatomical lumen.

15. The medical system of claim 14, wherein the endoscopic device is a tool used for ureteroscopy, hysteroscopy or colonoscopy.

16. The medical system of claim 11, wherein the first arm is coupled to a carriage that translates along the first rail portion.

17. The medical system of claim 11, wherein the first arm and the second arm are capable of extending upwardly over opposing sides of the bed.

18. The medical system of claim 11, further comprising:
a third arm attached to the first rail portion; and
a fourth arm attached to the second rail portion,
wherein the first to fourth arms are capable of manual and robotic control.

19. A medical system comprising:
a base;
a stand coupled to the base;
a bed supported by the stand;
a rail extending along the bed;
a first arm attached to the rail;
a second arm attached to the rail; and
control electronics configured to:
drive the first and second arms to move to a first configuration in which the first and second arms are positioned together along the rail for stowage, wherein the first arm and the second arm are stowed within a perimeter defined by the bed when viewed from above, and
drive the first and second arms to move to a second configuration in which the first and second arms are spaced apart along the rail to perform a medical procedure.

20. The medical system of claim 19, further comprising:
a first carriage supporting the first arm and slidingly attached to the rail portion; and
a second carriage supporting the second arm and slidingly attached to the rail portion,
wherein control electronics are further configured to:
drive the first and second carriages to slidingly translate to a position together on the rail portion to stow the first and second arms beneath the bed, and
drive the first and second carriages to slidingly translate to a position spaced apart on the rail portion to position the first and second arms for the medical procedure.

21. The medical system of claim 19, wherein the control electronics are further configured to:
drive first and second carriages to slidingly translate towards an end of the bed to stow the first and second arms beneath the bed, and
drive the first and second carriages to slidingly translate along a longitudinal side of the bed to perform the medical procedure.

* * * * *